United States Patent [19]

Brierley et al.

[11] Patent Number: 5,324,639

[45] Date of Patent: Jun. 28, 1994

[54] PRODUCTION OF INSULIN-LIKE GROWTH FACTOR-1 IN METHYLOTROPHIC YEAST CELLS

[75] Inventors: Russell A. Brierley; Geneva R. Davis; Gregory C. Holtz, all of San Diego, Calif.

[73] Assignee: The Salk Institute Biotechnology/Industrial Assoc, Inc., La Jolla, Calif.

[21] Appl. No.: 23,463

[22] Filed: Feb. 25, 1993

Related U.S. Application Data

[63] Continuation of Ser. No. 578,728, Sep. 4, 1990, abandoned.

[51] Int. Cl.$^5$ .............. C12P 21/06; C12N 1/16; C12N 15/00
[52] U.S. Cl. .............. 435/69.4; 536/23.5; 536/23.4; 536/23.51; 435/320.1; 435/69.1; 435/69.7; 435/69.8; 435/69.9; 435/254.23
[58] Field of Search .............. 435/69.4, 69.7, 69.8, 435/69.9, 69.1, 320.1, 255, 256, 172.3; 536/23.4, 23.5, 23.51

[56] References Cited

U.S. PATENT DOCUMENTS

| | | | |
|---|---|---|---|
| 4,837,148 | 6/1989 | Cregg et al. | 435/172.3 |
| 4,855,231 | 8/1989 | Stroman et al. | 435/68 |
| 4,882,279 | 11/1989 | Cregg | 435/172.3 |
| 4,895,800 | 1/1990 | Tschopp et al. | 435/69.3 |
| 4,929,555 | 6/1990 | Cregg et al. | 435/172.3 |

FOREIGN PATENT DOCUMENTS

| | | |
|---|---|---|
| 0123228 | 10/1984 | European Pat. Off. |
| 0128733 | 12/1984 | European Pat. Off. |
| 142268 | 5/1985 | European Pat. Off. |
| 0213593 | 3/1987 | European Pat. Off. |
| 0324274 | 12/1989 | European Pat. Off. |
| 173378 | 6/1991 | European Pat. Off. |
| WO84/03103 | 8/1964 | PCT Int'l Appl. |
| WO90/03431 | 4/1990 | World Int. Prop. O. |

OTHER PUBLICATIONS

Buckcholz, R. et al., *Bio/Technology*, 9: 1067–1072, 1991.
Elliott, S. et al., *Journal of Protein Chemistry*, 9(1):95–104, 1990.
Shuster, J. R., in *Yeast Genetic Engineering*, Barr et al., eds., Butterworth Publishers, Stoneham, Mass., pp. 85–108, 1989.
Kurtzman, C. P., *Antonie van Leeuwenhoek*, 50: 209–17, 1984.
Ellis, S. B. et al., *Mol. Cell. Biol.*, 5(5):1111–1121, 1985.
Sudberry, P. E. et al., *Biochemical Society Transactions*, 16: 1081–1083, 1988.
Gleeson, M. A. et al., *Yeast*, 4: 1–15, 1988.
Cregg, J. M. et al., *Biological Research on Industrial Yeast*, 2: 1–15, 1986.

(List continued on next page.)

*Primary Examiner*—Robert J. Hill, Jr.
*Assistant Examiner*—Marianne Porta Allen
*Attorney, Agent, or Firm*—Pretty, Schroeder, Brueggemann & Clark

[57] ABSTRACT

Insulin-like growth factor-1 (IGF-1), a naturally occurring, relatively short, single chain polypeptide, is prepared by growing methylotrophic yeast transformants containing in their genome at least one copy of a DNA sequence operably encoding IGF-1, in operational association with a DNA sequence encoding the *S. cerevisiae* alpha mating factor pre-pro sequence (including the proteolytic processing site: lys-arg), both under the regulation of a promoter region of a gene of a methylotrophic yeast, under conditions allowing expression of said DNA sequences, and secretion of IGF-1 into the culture medium.

Also disclosed are novel DNA fragments and novel recombinant yeast strains which are useful in the practice of the present invention.

31 Claims, 6 Drawing Sheets

OTHER PUBLICATIONS

Cregg, J. M. et al., *Developments in Industrial Microbiology*, 29: 33–41, 1988.

Creeg, J. M. in *Microbial Growth on $C_1$ Compounds*, van Verseveld, et al., eds, Martinus Nijhoff Publishers, Boston, pp. 158–167, 1987.

Komagata, K. in *Biology of Methylotrophs*, Goldberg et al., eds., Butterworth-Heinemann, Boston, pp. 25–37, 1991.

"The Amino Acid Sequence of Human Insulin-like Growth Factor-1 and its Structural Homology with Proinsulin", Rinderknecht, et al., *Thr Journal of Biological Chemistry*, 253:2769–2776 (1978).

"Sequence of cDNA encoding human insulin-like growth factor-1 precursor", Jansen, et al., *Nature*, 306:609–611 (1983).

"Efficient secretion and purification of human insulin-like growth factor-1 with a gene fusion vector in *Staphylococci*", Nilsson, et al., *Nucleic Acids Research*, 13:1151–1162 (1985).

"Expresssion of a biologically active analogue of somatomedin-C/insulin-like growth factor 1", Peters, et al., *Gene*, 35:83–89 (1985).

"Optimizing the expression in *E. coli* of a synthetic gene encoding somatomedin-C (IGF-1)", Buell, et al., *Nucleic Acids Research*, 13:1923–1938 (1985).

"Chemical Synthesis, Cloning and Expression of Genes for Human Somatomedin C (insulin-like Growth Factor 1) and $^{59}$Val-SomatomedinC", Niwa, et al., *Ann. NY Acad. Sci.*, 469:31–52 (1986).

"Expression purification and characterization of recombinant human insulin-like growth factor I in yeast", Bayne, et al., *Gene*, 66:235–244 (1988).

"Isolation and Characterization of a Glycosylated Form of Human Insulin-Like Growth Factor I Produced in *Saccharomyces cerevisiae*", Gellfors, et el., *The Journal of Biological Chemistry*, 264:11444–11449 (1989).

FIRST AMINO ACID OF
MATURE IGF-1
↓

```
      M  G  P  E  T  L  C  G  A  E  L  V  D  A  L  Q
AAGCTTACCTGCCATGGGACCGGAGACGCTCTGCGGGGCTGAGCTCGTGGATGCTCTGCA
HindIIIBspMINcoI                      SacI          PstI
TTCGAATGGACGGTACCCTGGCCTCTGCGAGACGCCCCGACTCGAGCACCTACGAGACGT
         10        20        30        40        50        60

F  V  C  G  D  R  G  F  Y  F  N  K  P  T  G  Y  G  S  S  S
GTTCGTGTGTGGAGACAGGGGCTTTTATTTCAACAAGCCCACAGGGTATGGCTCCAGCAG

CAAGCACACACCTCTGTCCCCGAAAATAAAGTTGTTCGGGTGTCCCATACCGAGGTCGTC
         70        80        90       100       110       120

R  R  A  P  Q  T  G  I  V  D  E  C  C  F  R  S  C  D  L  R
TCGACGGGCGCCTCAGACAGGCATCGTGGATGAGTGCTGCTTCCGGAGCTGTGATCTAAG
SalI                                      BspMII
AGCTGCCCGCGGAGTCTGTCCGTAGCACCTACTCACGACGAAGGCCTCGACACTAGATTC
        130       140       150       160       170       180

R  L  E  M  Y  C  A  P  L  K  P  A  K  S  A  *  *
GAGGCTCGAGATGTATTGCGCACCCCTCAAGCCTGCCAAGTCAGCTTGATAAGGATCCGA
    AvaI                                              BamHI
CTCCGAGCTCTACATAACGCGTGGGGAGTTCGGACGGTTCAGTCGAACTATTCCTAGGCT
        190       200       210       220       230       240

ATTC
EcoRI
TAAG
```

FIG. 1

PRODUCTION OF INSULIN-LIKE GROWTH FACTOR-1 IN METHYLOTROPHIC YEAST CELLS

This application is a continuation of U.S. application Ser. No. 07/578,728, filed Sep. 4, 1990, now abandoned.

FIELD OF THE INVENTION

This invention relates to a process of recombinant DNA technology for producing insulin-like growth factor-1 (IGF-1) peptides in methylotrophic yeast such as *Pichia pastoris*. The invention further relates to the methylotrophic yeast transformants, DNA fragments and expression vectors used for their production, and cultures containing same.

BACKGROUND OF THE INVENTION

Insulin-like growth factor-1 (IGF-1) is a polypeptide of 70 amino acids with a molecular weight of 7648 daltons. This single chain protein has three intrachain disulfide bridges. These disulfide bonds, along with numerous hydrogen bonds and hydrophilic interactions, maintain the compact tertiary structure of this molecule. However, Meng et al. [see *J. Chrom.*, 443: 183 (1988)] have shown that, upon reduction and reoxidation, IGF-1 can refold in a variety of ways, forming as many as 15 monomeric configurations. Consequently, attempts to produce this peptide by recombinant means in *E. coli* host expression systems provides a complicated mixture of product forms which must be purified for further use [see Grossgian and Friers in *Gene*, 18: 199 (1985)].

Insulin-like growth factor-1 belongs to a heterogeneous family of peptides which share some of the biological and chemical properties of insulin, but which are antigenically distinct from insulin. Currently available experimental evidence suggests that IGF-1 promotes growth by mediating the effects of growth hormone. Thus, such processes as skeletal growth, cell replication and other growth related processes are affected by IGF-1 levels.

Physiological concentrations of IGF-1 have been shown to be influenced by such conditions as thyroid disease, diabetes and malnutrition [see Preece, in *Horm. Blood*, 4: 108 (1983)]. IGF-1 has also been shown to act synergistically with other growth factors, for example, in accelerating the healing of soft and mesenchymal tissue wounds [see Lynch et al., in *J. Clin. Periodontol.*, 16: 545 (1989) and Lynch et al., in *Proc. Natl. Acad. Sci. USA*, 84: 7696 (1987)], and in enhancing the growth of mammalian cells in serum-free tissue culture medium [see Burleigh and Meng, in *American Biotech. Lab.*, 4: 48 (1986)].

Considering the many clinical and research applications of IGF-1, a ready supply of IGF-1, such as that which would result from fermentation of IGF-1 expressing recombinant organisms, will be of great value to the medical and biotechnology fields.

Since isolation from natural sources is technically difficult, expensive, and time consuming, recent efforts have centered on the development of efficient recombinant methods for the production of IGF-1.

Of the hosts widely used for the production of heterologous proteins, probably *E. coli* and *Saccharomyces cerevisiae* (Baker's yeast) are the best understood. However, *E. coli* does not possess the ability to produce disulfide bonds in proteins, thus proteins such as IGF-1 frequently are not stable in the presence of endogenous bacterial proteases, and tend to aggregate into inactive complexes. As a result of this inability to produce disulfide bonds, IGF-1 produced in *E. coli* has to be extracted and then the disulfide bonds have to be formed by oxidation. This results in a complicated mixture of 15 different forms of IGF-1, which must be separated. Consequently, the yield of purified product is very low (Grossgian and Friers, supra). Furthermore, in order to produce in *E. coli* IGF-1 molecules which contain the authentic N-terminal amino acid, i.e., glycine, and not the initiating methionine present on the primary translation product, it is necessary to express IGF-1 in *E. coli* as a fusion protein. Cleavage of mature IGF-1 from the initially produced fusion protein necessitates an additional step in the production process.

Yeasts can offer clear advantages over bacteria in the production of heterologous proteins, which include their ability to secrete heterologous proteins into the culture medium. Secretion of proteins from cells is generally superior to production of proteins in the cytoplasm. Secreted products are obtained in a higher degree of initial purity; and further purification of the secreted products is made easier by the absence of cellular debris. In the case of sulfhydryl-rich proteins, there is another compelling reason for the development of eukaryotic hosts capable of secreting such proteins into the culture medium: their correct tertiary structure is produced and maintained via disulfide bonds. This is because the secretory pathway of the cell and the extracellular medium are oxidizing environments which can support disulfide bond formation [Smith, et al., *Science*, 229: 1219 (1985)]; whereas, in contrast, the cytoplasm is a reducing environment in which disulfide bonds cannot form. Upon cell breakage, too rapid formation of disulfide linkages can result in random disulfide bond formation. Consequently, production of sulfhydryl-rich proteins, such as IGF-1, containing appropriately formed disulfide bonds, can potentially be best achieved by transit through the secretory pathway.

Gellerfors et al., in *J. Biol. Chem.*, 264: 11444–11449 (1989), describe the production of IGF-1 in *S. cerevisiae* under the control of the *S. cerevisiae* actin promoter. The IGF-1 product is encoded by autonomously replicating plasmid-borne DNA. In a similar study, Bayne et al., in *Gene*, 66: 235–244 (1988), describe the production of IGF-1 in *S. cerevisiae* under the control of the *S. cerevisiae* alpha mating factor promoter. The latter authors report yields of IGF-1 which are quite low, with production of only about 2 mg of IGF-1 per liter of fermentation broth being reported.

In view of the problems usually encountered with up-scaling the production of heterologous proteins in autonomous plasmid-based yeast systems, such as *S. cerevisiae*, and the difficulties observed in reported work in *S. cerevisiae*, no motivation is provided by the art for one to further pursue the production of IGF-1 in *S. cerevisiae*.

To overcome the major problems associated with the expression of recombinant gene products in *S. cerevisiae* (e.g., loss of selection for plasmid maintenance and problems concerning plasmid distribution, copy number and stability in fermentors operated at high cell density), a yeast expression system based on methylotrophic yeast, such as for example, *Pichia pastoris*, has been developed. A key feature of this unique system lies with the promoter employed to drive heterologous gene expression. This promoter, which is derived from a methanol-responsive gene of a methylotrophic yeast, is frequently highly expressed and tightly regulated (see, e.g., European Patent Application No. 85113737.2, published Jun. 4, 1986, under No. 0 183 071, now issued in the United States as U.S. Pat. No. 4,855,231). Another key feature of expression systems based on methylotrophic yeast is the ability of expression cassettes to stably integrate into the genome of the methylotrophic yeast host, thus significantly decreasing the chance of vector loss.

Although the methylotrophic yeast, *P. pastoris*, has been used successfully for the production of various heterologous proteins, e.g., hepatitis B surface antigen [Cregg et al., *Bio/Technology* 5, 479 (1987)], lysozyme and invertase [Digan et al., *Developments in Industrial Microbiology* 29: 59 (1988); Tschopp et al., *Bio/Technology* 5: 1305 (1987)], endeavors to produce other heterologous gene products in *Pichia*, especially by secretion, have given mixed results. At the present level of understanding of methylotrophic yeast expression systems, it is unpredictable whether a given gene can be expressed to an appreciable level in such yeast or whether the yeast host will tolerate the presence of the recombinant gene product in its cells. Further, it is especially difficult to foresee if a particular protein will be secreted by the methylotrophic yeast host, and if it is, at what efficiency. Even for the non-methylotrophic yeast, *S. cerevisiae*, which has been considerably more extensively studied than *P. pastoris*, the mechanism of protein secretion is not well defined and understood.

SUMMARY OF THE INVENTION

In accordance with the present invention, we have developed an expression system suitable for the production of biologically active insulin-like growth factor-1 (IGF-1) molecules. The present invention provides a powerful method for the production of secreted IGF-1 peptides in methylotrophic yeast. In addition, the invention method can easily be scaled up from shake-flask cultures to large scale fermentors with no loss in IGF-1 productivity. Moreover, the invention method can readily be scaled up without the need for making major changes in the fermentation conditions used for the growth of the transformed strains, relative to the conditions used for the small scale growth of transformed strains.

We have surprisingly found that IGF-1 peptides can very efficiently be produced in, and secreted from, methylotrophic yeast, such as, for example, *P. pastoris*. This is accomplished by transforming a methylotrophic yeast with, and preferably integrating into the yeast genome, at least one copy of a first DNA sequence operably encoding an IGF-1 peptide, wherein said first DNA sequence is operably associated with a second DNA sequence encoding the *S. cerevisiae* alpha-mating factor (AMF) pre-pro sequence (including the proteolytic processing site: lys-arg), and wherein both of said DNA sequences are under the regulation of a methanol responsive promoter region of a gene of a methylotrophic yeast. Methylotrophic yeast cells containing in their genome at least one copy of these DNA sequences efficiently produce and secrete biologically active IGF-1 peptides into the medium.

The present invention is directed to the above aspects and all associated methods and means for accomplishing such. For example, the invention includes the technology requisite to suitable growth of the methylotrophic yeast host cells, fermentation, and isolation and purification of the IGF-1 gene product.

BRIEF DESCRIPTION OF THE DRAWINGS

FIG. 1 provides the nucleotide sequence of a synthetic insulin-like growth factor gene.

DETAILED DESCRIPTION OF THE INVENTION

Figure 2:
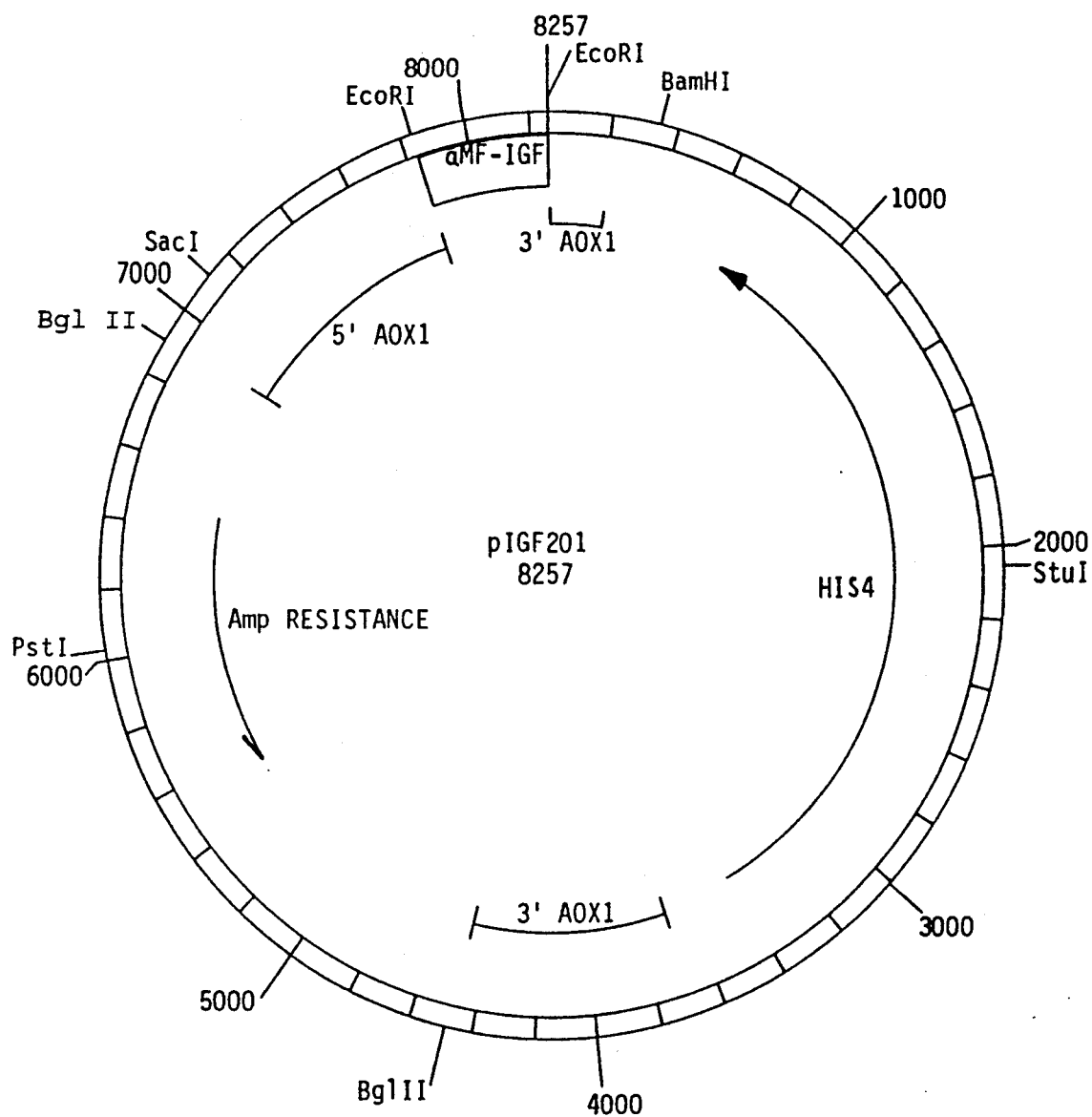
FIG. 2 is a restriction map of plasmid pIGF201.

In accordance with the present invention, there is provided a DNA fragment containing at least one copy of an expression cassette comprising, in the reading frame direction of transcription, the following DNA sequences:
(i) a promoter region of a methanol responsive gene of a methylotrophic yeast,
(ii) a DNA sequence encoding a polypeptide consisting of:
  (a) the *S. cerevisiae* AMF pre-pro sequence, including the proteolytic processing site: lys-arg, and
  (b) an insulin-like growth factor-1 (IGF-1) peptide; and
(iii) a transcription terminator functional in a methylotrophic yeast, wherein said DNA sequences are operationally associated with one another for transcription of the sequences encoding said polypeptide.

The DNA fragment according to the invention can be transformed into methylotrophic yeast cells as a linear fragment flanked by DNA sequences having sufficient homology with a target gene to effect integration of said DNA fragment therein. In this case integration takes place by replacement at the site of the target gene. Alternatively, the DNA fragment can be part of a circular plasmid, which may be linearized to facilitate integration, and will integrate by addition at a site of homology between the host and the plasmid sequence.

In accordance with another embodiment of the present invention, there is provided an expression vector containing at least one copy of an expression cassette as described hereinabove.

According to another aspect of the present invention, there are provided novel methylotrophic yeast cells containing in their genome at least one copy of the above described DNA fragment.

According to a still further embodiment of the present invention, there is provided a process for producing IGF-1 peptides by growing methylotrophic yeast transformants containing in their genome at least one copy of a DNA sequence operably encoding an IGF-1 peptide, operably associated with DNA encoding the *S. cerevisiae* AMF pre-pro sequence (including the lys-arg proteolytic processing site), both under the regulation of a promoter region of a methanol responsive gene of a methylotrophic yeast, under conditions allowing the expression of said DNA sequence in said transformants and secreting IGF-1 peptides into the culture medium. Cultures of viable methylotrophic yeast cells capable of producing IGF-1 peptides are also within the scope of the present invention.

The polypeptide product produced in accordance with the present invention is secreted to the culture medium at surprisingly high concentrations; the level of IGF-1 peptides secretion is up to 2 orders of magnitude (i.e., up to 100 times) higher than the *S. cerevisiae* results published in the literature (see Bayne et al., supra). In addition to the unique properties of the invention expression system, the excellent results obtained in the practice of the present invention are also due to the fact that the *S. cerevisiae* alpha-mating factor pre-pro sequence functions unexpectedly well to direct secretion of IGF-1 peptides in methylotrophic yeast.

The term "insulin-like growth factor-1" or "IGF-1 peptide" or simply "IGF-1", as used throughout the specification and in the claims, refers to a polypeptide product which exhibits similar, in-kind, biological activities to natural insulin-like growth factor-1, as measured in recognized bioassays, and has substantially the same amino acid sequence as native IGF-1 (see FIG. 1). It will be understood that polypeptides deficient in one or more amino acids in the amino acid sequence reported in the literature for naturally occurring IGF-1, or polypeptides containing additional amino acids or polypeptides in which one or more amino acids in the amino acid sequence of natural IGF-1 are replaced by other amino acids are within the scope of the invention, provided that they exhibit the functional activity of IGF-1, e.g., by acting synergistically with other growth factors in accelerating the healing of soft and mesenchymal tissue wounds. The invention is intended to embrace all the allelic variations of IGF-1. Moreover, as noted above, derivatives obtained by simple modification of the amino acid sequence of the naturally occurring product, e.g, by way of site-directed mutagenesis or other standard procedures, are included within the scope of the present invention. Forms of IGF-1 produced by proteolysis of host cells that exhibit similar biological activities to mature, naturally occurring IGF-1 are also encompassed by the present invention.

The amino acids which occur in the various amino acid sequences referred to in the specification have their usual, three- and one-letter abbreviations, routinely used in the art, i.e.:

| Amino Acid | Abbreviation | |
|---|---|---|
| L-Alanine | Ala | A |
| L-Arginine | Arg | R |
| L-Asparagine | Asn | N |
| L-Aspartic acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

According to the present invention, IGF-1 peptides are produced by methylotrophic yeast cells containing in their genome at least one copy of a DNA sequence operably encoding IGF-1 peptides operably associated with DNA encoding the *S. cerevisiae* α-mating factor (AMF) pre-pro sequence (including the proteolytic processing site: lys-arg) under the regulation of a promoter region of a methanol responsive gene of a methylotrophic yeast.

The term "a DNA sequence operably encoding IGF-1 peptides" as used herein includes DNA sequences encoding IGF-1 or any other "IGF-1 peptide" as defined hereinabove. DNA sequences encoding IGF-1 are known in the art. They may be obtained by chemical synthesis or by transcription of messenger RNA (mRNA) corresponding to IGF-1 into complementary DNA (cDNA) and converting the latter into a double stranded cDNA. Chemical synthesis of a gene for human IGF-1 is, for example, disclosed by Niwa et al., in *Annals of the NY Academy of Science*, 469: 31-52 (1986), or Buell et al., in *Nucleic Acids Research*, 13: 1923-1938 (1985). The requisite DNA sequence can also be removed, for example, by restriction enzyme digest of known vectors harboring the IGF-1 gene. Examples of such vectors and the means for their preparation can be taken from various publications, such as, for example, the Niwa or Buell disclosures referred to above. The nucleotide sequence of a presently preferred IGF-1 gene used in accordance with the present invention is illustrated in FIG. 1 and is further elucidated in the examples.

Yeast species contemplated for use in the practice of the present invention are methylotrophs, i.e., species which are able to grow on methanol (as well as other) carbon source nutriment. Species which have the biochemical pathways necessary for methanol utilization fall into four genera, i.e., *Candida, Hansenula, Pichia,* and *Torulopsis*. Of these, a substantial amount is known about the molecular biology of members of the species *Hansenula polymorpha* and *Pichia pastoris.*

The presently preferred yeast species for use in the practice of the present invention is *Pichia pastoris*, a known industrial yeast strain that is capable of efficiently utilizing methanol as the sole carbon and energy source.

There are a number of methanol responsive genes in methylotrophic yeast, the expression of each being controlled by methanol responsive regulatory regions (also referred to as promoters). Any of such methanol responsive promoters are suitable for use in the practice of the present invention. Examples of specific regulatory regions include the promoter for the primary alcohol oxidase gene from *Pichia pastoris* AOX1, the promoter for the secondary alcohol oxidase gene from *P. pastoris* AOX2, the promoter for the dihydroxyacetone synthase gene from *P. pastoris* (DAS), the promoter for the P40 gene from *P. pastoris,* the promoter for the catalase gene from *P. pastoris,* and the like.

The presently preferred promoter region employed to drive IGF-1 gene expression is derived from a methanol-regulated alcohol oxidase gene of *P. pastoris. P. pastoris* is known to contain two functional alcohol oxidase genes: alcohol oxidase I (AOX1) and alcohol oxidase II (AOX2) genes. The coding portions of the two AOX genes are closely homologous at both the DNA and the predicted amino acid sequence levels and share common restriction sites. The proteins expressed from the two genes have similar enzymatic properties but the promoter of the AOX1 gene is more efficient and more highly expressed; therefore, its use is preferred for IGF-1 expression. The AOX1 gene, including its promoter, has been isolated and thoroughly characterized; see Ellis et al., *Mol. Cell. Biol.* 5: 1111 (1985) and U.S. Pat. No. 4,855,231.

The expression cassette used for transforming methylotrophic yeast cells contains, in addition to a methanol responsive promoter of a methylotrophic yeast gene and the IGF-1 encoding DNA sequence (IGF-1 gene), a DNA sequence encoding the in-reading frame S. cerevisiae AMF pre-pro sequence, including a DNA sequence encoding the processing site: lys-arg (also referred to as the lys-arg encoding sequence), and a transcription terminator functional in a methylotrophic yeast.

The S. cerevisiae alpha-mating factor is a 13-residue peptide, secreted by cells of the "alpha" mating type, that acts on cells of the opposite "a" mating type to promote efficient conjugation between the two cell types and thereby formation of "a-alpha" diploid cells [Thorner et al., The Molecular Biology the Yeast Saccharomyces, Cold Spring Harbor Laboratory, Cold Spring Harbor, N.Y., 143 (1981)]. The AMF pre-pro sequence is a leader sequence contained in the AMF precursor molecule, and includes the lys-arg encoding sequence which is necessary for proteolytic processing and secretion (see, e.g., Brake et al., Proc. Natl. Acad. Sci. USA, 81: 4642 (1984)).

The transcription terminator functional in a methylotrophic yeast used in accordance with the present invention has either (a) a subsegment which encodes a polyadenylation signal and polyadenylation site in the transcript, and/or (b) a subsegment which provides a transcription termination signal for transcription from the promoter used in the expression cassette. The term "expression cassette" as used herein, and throughout the specification and claims, refers to a DNA sequence which includes sequences functional for both the expression and the secretion processes. The entire transcription terminator is taken from a protein-encoding gene, which may be the same or different from the gene which is the source of the promoter.

For the practice of the present invention it is preferred that multiple copies of the above-described expression cassettes be contained on one DNA fragment, preferably in a head-to-tail orientation.

The DNA fragments according to the invention optionally further comprise a selectable marker gene. For this purpose, any selectable marker gene functional in methylotrophic yeast may be employed, i.e., any gene which confers a phenotype upon methylotrophic yeast cells, thereby allowing them to be identified and selectively grown from among a vast majority of untransformed cells. Suitable selectable marker genes include, for example, selectable marker systems composed of an auxotrophic mutant P. pastoris host strain and a wild type biosynthetic gene which complements the host's defect. For transformation of His4− P. pastoris strains, for example, the S. cerevisiae or P. pastoris HIS4 gene, or for transformation of Arg4− mutants, the S. cerevisiae ARG4 gene or the P. pastoris ARG4 gene, may be employed.

In addition, DNA fragments according to the invention optionally further comprise selectable marker genes which are functional in bacteria. Thus, any gene can be used which confers a phenotype on bacteria that allows transformed bacterial cells to be identified and selectively grown from among a vast majority of untransformed cells. This additional selectable marker enables DNA of the invention to be transformed into bacteria such as E. coli for amplification. Suitable selectable marker genes include the ampicillin resistance gene (Amp$^r$), tetracycline resistance gene (Tc$^r$), and the like.

When it is contemplated to pass DNA of the invention through bacterial cells, it is desirable to include in the DNA construct a bacterial origin of replication, to ensure the maintenance of the invention DNA from generation to generation of the bacteria. Exemplary bacterial origins of replication include the f1-ori, colisin, col E1, and the like.

If the yeast host is transformed with a linear DNA fragment containing the IGF-1 gene under the regulation of a promoter region of a P. pastoris gene and AMF sequences necessary for processing and secretion, the expression cassette is integrated into the host genome by any of the gene replacement techniques known in the art, such as by one-step gene replacement [see e.g., Rothstein in Methods Enzymol. 101: 202 (1983); Cregg et al. in Bio/Technology 5: 479 (1987) or U.S. Pat. No. 4,882,279] or by two-step gene replacement methods [see e.g., Scherer and Davis in Proc. Natl. Acad. Sci. USA, 76: 4951 (1979)]. The linear DNA fragment is directed to the desired locus, i.e., to the target gene to be disrupted, by means of flanking DNA sequences having sufficient homology with the target gene to effect integration of the DNA fragment therein. One-step gene disruptions are usually successful if the DNA to be introduced has as little as 0.2 kb homology with the fragment locus of the target gene; it is however, preferable to maximize the degree of homology for efficiency.

If the DNA fragment according to the invention is contained within, or is an expression vector, e.g., a circular plasmid, one or more copies of the plasmid can be integrated at the same or different loci, by addition to the genome instead of by gene disruption. Linearization of the plasmid by means of a suitable restriction endonuclease facilitates integration.

The term "expression vector" as employed herein, is intended to include vectors capable of expressing DNA sequences contained therein, where such sequences are in operational association with other sequences capable of effecting their expression, i.e., promoter sequences. In general, expression vectors usually used in recombinant DNA technology are often in the form of "plasmids" i.e., circular double-stranded DNA loops, which in their vector form are not bound to the chromosome. In the present specification the terms "vector" and "plasmid" are used interchangeably. However, the invention is intended to include other forms of expression vectors as well, which function equivalently.

In the DNA fragments of the present invention, the segments of the expression cassette(s) are said to be "operationally associated" with one another. The DNA sequence encoding IGF-1 peptides is positioned and oriented functionally with respect to the promoter, the DNA sequence encoding the S. cerevisiae AMF pre-pro sequence (including the DNA sequence encoding the AMF processing-site: lys-arg), and the transcription terminator. Thus, the polypeptide encoding segment is transcribed, under regulation of the promoter region, into a transcript capable of providing, upon translation, the desired polypeptide. Because of the presence of the AMF pre-pro sequence, the expressed IGF-1 product is found as a secreted entity in the culture medium. Appropriate reading frame positioning and orientation of the various segments of the expression cassette are within the knowledge of persons of ordinary skill in the art; further details are given in the Examples.

The DNA fragment provided by the present invention may include sequences allowing for its replication and selection in bacteria, especially In this way, large quantities of the DNA fragment can be produced by replication in bacteria.

Methods of transforming methylotrophic yeast, such as, for example, *Pichia pastoris*, as well as methods applicable for culturing methylotrophic yeast cells containing in their genome a gene encoding a heterologous protein, are known generally in the art.

According to the invention, the expression cassettes are transformed into methylotrophic yeast cells either by the spheroplast technique, described by Cregg et al. in *Mol. Cell. Biol.* 5: 3376 (1985) and U.S. Pat. No. 4,879,231, or by the whole-cell lithium chloride yeast transformation system [Ito et al., *Agric. Biol. Chem.* 48: 341 (1984)], with modification necessary for adaptation to methylotrophic yeast, such as *P. pastoris* [See European Patent Application No. 312,934; also available as U.S. Pat. No. 4,929,555]. The whole-cell lithium chloride method is frequently more convenient in that it does not require the generation and maintenance of spheroplasts. However, for the purpose of the present invention the spheroplast method is preferred, because the spheroplast method is generally more efficient with linear DNA.

Positive transformants are characterized by Southern blot analysis [Maniatis et al., *Molecular Cloning: A Laboratory Manual*, Cold Spring Harbor Laboratory Press, Cold Spring Harbor, N.Y., USA (1982)] for the site of DNA integration; Northern blots [Maniatis, *Op. Cit.*, R. S. Zitomer and B. D. Hall, *J. Biol. Chem*, 251: 6320 (1976)] for methanol-responsive IGF-1 gene expression; and product analysis for the presence of secreted IGF-1 peptides in the growth media.

Transformed strains, which are of the desired phenotype and genotype, are grown in fermentors. For the large-scale production of recombinant DNA-based products in methylotrophic yeast, a three-stage, high cell-density, fed batch fermentation system is normally the preferred fermentation protocol employed. In the first, or growth stage, expression hosts are cultured in defined minimal medium with an excess of a non-inducing carbon source (e.g., glycerol). When grown on such carbon sources, heterologous gene expression is completely repressed, which allows the generation of cell mass in the absence of heterologous protein expression. It is presently preferred, during this growth stage, that the pH of the medium be maintained at about 5. Next, a short period of non-inducing carbon source limitation growth is allowed to further increase cell mass and derepress the methanol responsive promoter. The pH of the medium during this limitation growth period is adjusted to the pH value to be maintained during the production phase, which is generally carried out below a pH of about 4; preferably at a pH in the range of about 2-3.5. Subsequent to the period of growth under limiting conditions, methanol alone (referred to herein as "methanol excess fed-batch mode") or a limiting amount of a non-inducing carbon source plus and methanol (referred to herein as "mixed-feed fed-batch mode") are added in the fermentor, inducing the expression of the IGF-1 gene driven by a methanol responsive promoter. This third stage is the so-called production stage.

The term "culture" means a propagation of cells in a medium conducive to their growth, and all subcultures thereof. The term "subculture" refers to a culture of cells grown from cells of another culture (source culture), or any subculture of the source culture, regardless of the number of subculturings which have been performed between the subculture of interest and the source culture.

According to a preferred embodiment of the present invention, the heterologous protein expression system used for IGF-1 production utilizes the promoter derived from the methanol-regulated AOX1 gene of *P. pastoris*, which is very efficiently expressed and tightly regulated. This gene can be the source of the transcription terminator as well. The presently preferred expression cassette comprises, operationally associated with one another, the *P. pastoris* AOX1 promoter, DNA encoding the *S. cerevisiae* AMF pre-pro sequence (including the DNA sequence encoding the AMF processing site: lys-arg), a DNA sequence encoding mature IGF-1, and a transcription terminator derived from the *P. pastoris* AOX4 gene. Preferably, two or more of such expression cassettes are contained on one DNA fragment, in head-to-tail orientation, to yield multiple expression cassettes on a single contiguous DNA fragment. The presently preferred host cells to be transformed with multiple expression cassettes are *P. pastoris* cells having at least one mutation that can be complemented with a marker gene present on a transforming DNA fragment. Preferably His4− (GS115) or Arg4− (GS190) auxotrophic mutant *P. pastoris* strains are employed.

The fragment containing one or more expression cassette(s) is inserted into a plasmid containing a marker gene complementing the host's defect, and optionally containing additional sequences such as bacterial marker genes, yeast sequences which direct vector integration, and the like. pBR322-based plasmids, e.g., pAO815, are preferred. Insertion of one or more copies of the IGF-1 expression/secretion cassette into parent plasmid pAO815 produces plasmids such as pIGF201, pIGF202, pIGF204, pIGF206, and the like.

To develop Mut− expression strains of *P. pastoris* (Mut refers to the methanol-utilization phenotype), the transforming DNA comprising the expression cassette(s) is preferably integrated into the host genome by a one-step gene replacement technique. The expression vector is digested with an appropriate enzyme to yield a linear DNA fragment with ends homologous to the AOX1 locus by means of the flanking homologous sequences. This approach avoids the problems encountered with *S. cerevisiae*, wherein expression cassettes must be present on multicopy plasmids to achieve high level of expression. As a result of gene replacement, Mut− strains are obtained. In Mut− strains, the AOX1 gene is replaced with the expression cassette(s), thus decreasing the strains' ability to utilize methanol. A slow growth rate on methanol is maintained by expression of the AOX2 gene product. The transformants in which the expression cassette has integrated into the AOX1 locus by site-directed recombination can be identified by first screening for the presence of the complementing gene. This is preferably accomplished by growing the cells in media lacking the complementing gene product and identifying those cells which are able to grow by nature of expression of the complementing gene. Next, the selected cells are screened for their Mut phenotype by growing them in the presence of methanol and monitoring their growth rate.

To develop Mut+ IGF-1-expressing strains, the fragment comprising one or more expression cassette(s) preferably is integrated into the host genome by transformation of the host with a circular plasmid or a linearized plasmid comprising the expression cassette(s). The integration is by addition at a locus or loci having homology with one or more sequences present on the transformation vector.

Positive transformants are characterized by Southern analysis for the site of DNA integration; by Northern analysis for methanol-responsive IGF-1 gene expression; and by product analysis for the presence of secreted IGF-1 peptides in the growth media.

Methylotrophic yeast transformants which are identified to have the desired genotype and phenotype are grown in fermentors. It is presently preferred to use the three-step production process described above. The level of IGF-1 secreted into the media can be determined by Western blot analysis of the media in parallel with an IGF-1 standard, using anti-IGF-1 antisera; by radioimmunoassay (RIA); by radio receptor assay; or by HPLC after suitable pretreatment of the medium.

The invention will now be described in greater detail with reference to the following non-limiting examples.

EXAMPLES

P. pastoris is described herein as a model system for the use of methylotrophic yeast hosts. Other useful methylotrophic yeasts can be taken from four genera, namely Candida, Hansenula, Pichia and Torulopsis. Equivalent species from them may be used as hosts herein primarily based upon their demonstrated characterization of being supportable for growth and exploitation on methanol as a single carbon nutriment source. See, for example, Gleeson et al., Yeast 4: 1 (1988).

EXAMPLE 1:

Construction of IGF-1 encoding expression vectors

The expression vector constructions described in the present application are performed using standard procedures, as described, for example in Maniatis et al., Supra, and Davis et al., Basic Methods in Molecular Biology, Elsevier Science Publishing, Inc., New York a. Single copy vector pIGF201

The synthetic gene encoding human IGF-1 shown in FIG. 1 (as a HindIII-BamHI fragment), incorporated in vector pUC18, was used to transform E. coil strain MC1061. Ampicillin-resistant transformants were selected and screened by examination of restriction enzyme-digested DNA for the presence of a HindIII-BamHI insert of approximately 240 bp, the size expected for the IGF-1 gene. One transformant with an insert of this size was used to prepare plasmid DNA (pIGF101).

The 240 bp HindIII-BamHI fragment (250 ng) isolated from pIGF101, containing the IGF-1 gene, was inserted into the HindIII-BamHI site of plasmid pAO203 (10 ng; the construction of pAO203 is described in Example 5). Plasmid pAO203 contains the DNA sequence encoding the αMF pre-pro region (with an EcoRI site at the 5' end) followed by nucleotides which encode the amino acids for three processing sites, lys-arg and (glu-ala)$_2$ (with a HindIII site at the 3' end). The resulting plasmid was used to transform E. coli MC1061 cells. Ampicillin-resistant colonies were selected and screened with an oligonucleotide complementary to sequence 162 to 132 of the IGF-1 gene (see FIG. 1). One colony which was positive in this screen was chosen as a source of the αMF-IGF-1 fusion gene-containing plasmid designated pIGF102.

The EcoRI-BamHI fragment from pIGF102 (250 ng), containing the αMF pre-pro region and proteolytic processing sites, and IGF-1 gene, was cloned into M13mp19 (10 ng) and used to transform E. coli JM103 cells. The resultant transformants were screened by analysis of restriction enzyme-digested DNA, and one clone (pIGF103) with an insert of the correct size (480 bp EcoRI-BamHI fragment) was used to prepare single-stranded DNA.

Site-directed mutagenesis of the single-stranded DNA was performed to delete the (glu-ala)$_2$ processing sites, the HindIII cloning site, the polylinker attached to the synthetic gene, and the codon for the initial methionine of IGF-1. Mutagenesis was accomplished using standard procedures and oligos having the following sequences:

mutagenizing oligo:

5'-GTATCTTTGGATAAAAGAGGACC-
GGAGACGCTCTGC-3' screening oligo:

5'-ATAAAAGAGGACCGGA-3'

Removal of the above noted sequences yielded a fusion gene consisting of the DNA sequence encoding the αMF pre-pro region and lys-arg processing sites fused directly to the coding region of the IGF-1 gene. The presence of only one processing site (lys-arg), achieved by deletion of the (glu-ala)$_2$ processing sites, provided for more efficient processing of the precursor protein. The mutagenized clone was sequenced to verify the changes and then subjected to a second site-directed mutagenesis to insert an EcoRI site immediately following the translation termination codon of the IGF-1 gene. Oligonucleotides having sequences as follows were used in this mutagenesis:

mutagenizing oligo:

5'-AGTCAGCTTGATAAGAATTCAAAT-
GAGTCGACCTGCAGGC-3' screening oligo:

5'-TAAGAATTCAAATGAGT-3'

After the second mutagenesis was confirmed by DNA sequencing, the αMF-IGF-1 gene fusion was isolated on a 450 bp EcoRI fragment, then 250 ng of this EcoRI fragment was inserted into 10 ng of the P. pastoris expression vector pAO815 (which had been previously digested with EcoRI and treated with calf alkaline phosphatase). The construction of pAO815 is described in Example 6. The resulting single-copy expression vector, pIGF201, contains one copy of the αMF-IGF-1 fusion gene under the transcriptional control of the Pichia pastoris AOX1 promoter and regulatory regions, as well as the AOX1 transcription termination and polyadenylation signals. In addition, the vector includes the Pichia pastoris HIS4 gene used for selection in His$^-$ hosts and additional 3' AOX1 sequences which can be used to direct integration of the vector into the host genome. Plasmid pIGF201 is shown in FIG. 2.

The entire αMF-IGF-1 fusion gene and approximately 50 nucleotides each of the promoter and termination regions of pIGF201 were sequenced to verify that the nucleotide sequences were not altered during the cloning process.

b. Multi-copy vectors pIGF202, pIGF204, pIGF206

Figure 3:
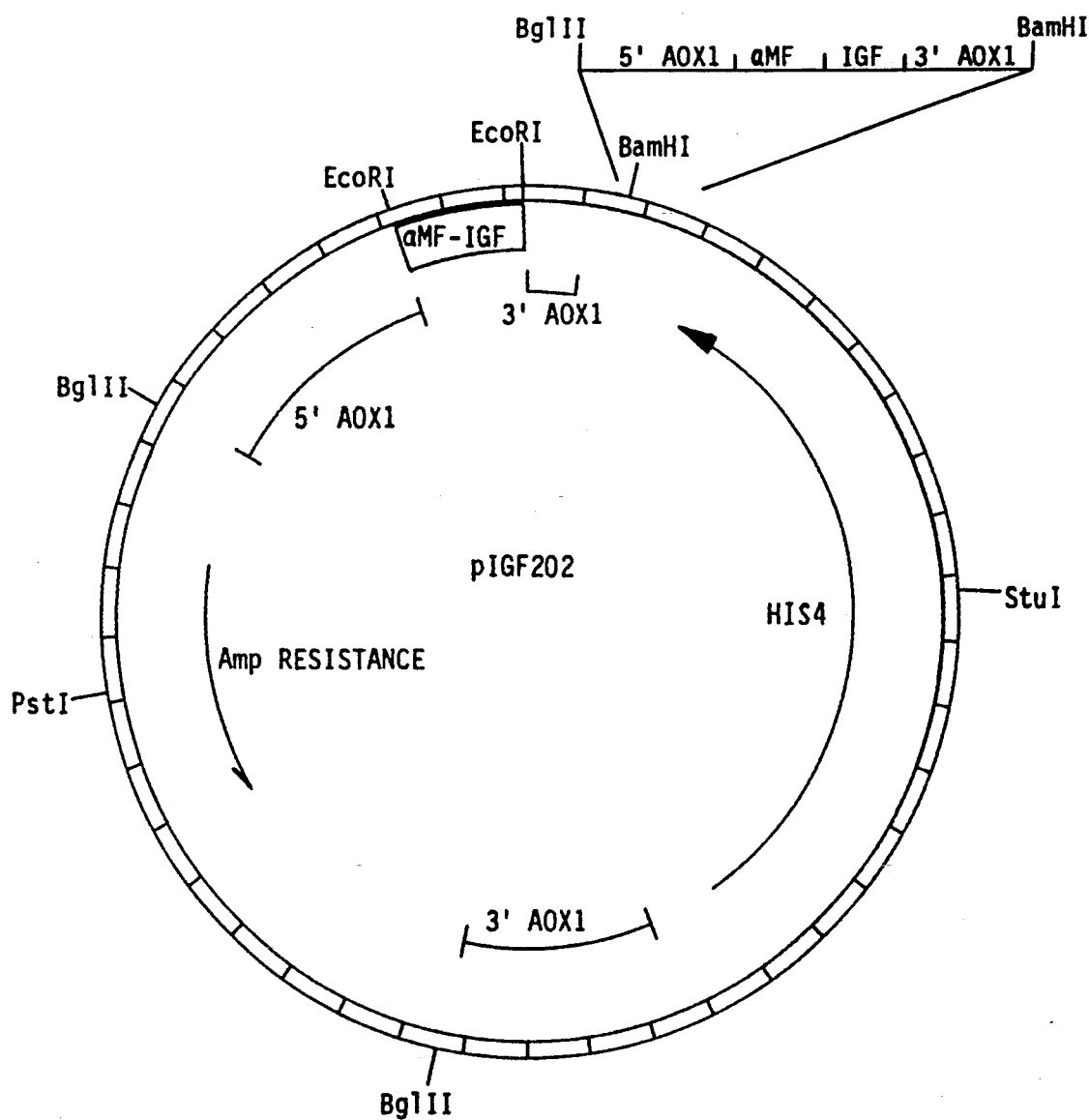
FIG. 3 is a restriction map of plasmid pIGF202.

The expression cassette containing the AOX1 promoter and regulatory region, the αMF-IGF-1 fusion gene, and the AOX1 transcription termination and polyadenylation signals was isolated from pIGF201 as a 1700 bp BglII-BamHI fragment. The BglII-BamHI expression cassette (250 ng) was inserted back into the unique BamHI site of pIGF201 (10 ng of BamHI digested, calf alkaline phosphatase-treated pIGF201). MC1061 cells were transformed with the ligation. Amp$^R$ colonies were selected and plasmid was characterized by restriction digest. Analysis of restriction enzyme digests of the resulting plasmid, pIGF202 (see FIG. 3), verified that the two expression cassettes were joined as tandem-repeat units rather than inverted-repeat units: SalI digest yielded ~2100, 1750, and 6100 bp bands; ClaI/BamHI digest yielded ~3800 and 6450 bp bands.

Figure 4:
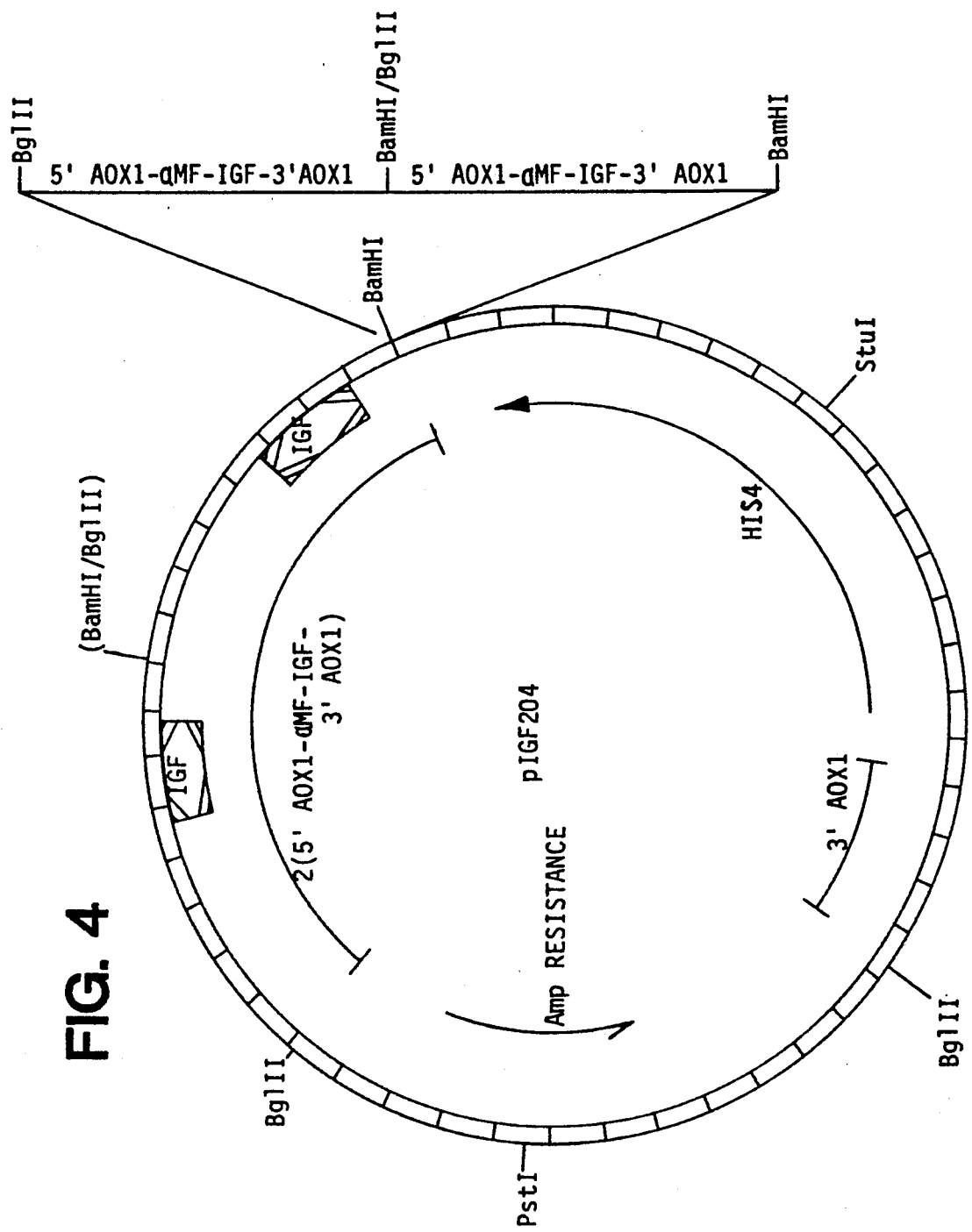
FIG. 4 is a restriction map of plasmid pIGF204.

The BglII-BamHI fragment from plasmid pIGF202, containing two copies of the expression cassette, was isolated (250 ng) and inserted back into the unique BamHI site in calf alkaline phosphatase-treated pIGF202 (10 ng) to yield vector pIGF204 (see FIG. 4), containing four copies of the expression cassette. MC1061 cells were transformed with the ligation. Amp$^R$ colonies were selected and plasmid was characterized by restriction digest. Correct plasmid demonstrated ~6600 and 6900 bp bands upon digestion with ClaI and BamHI.

Figure 5:
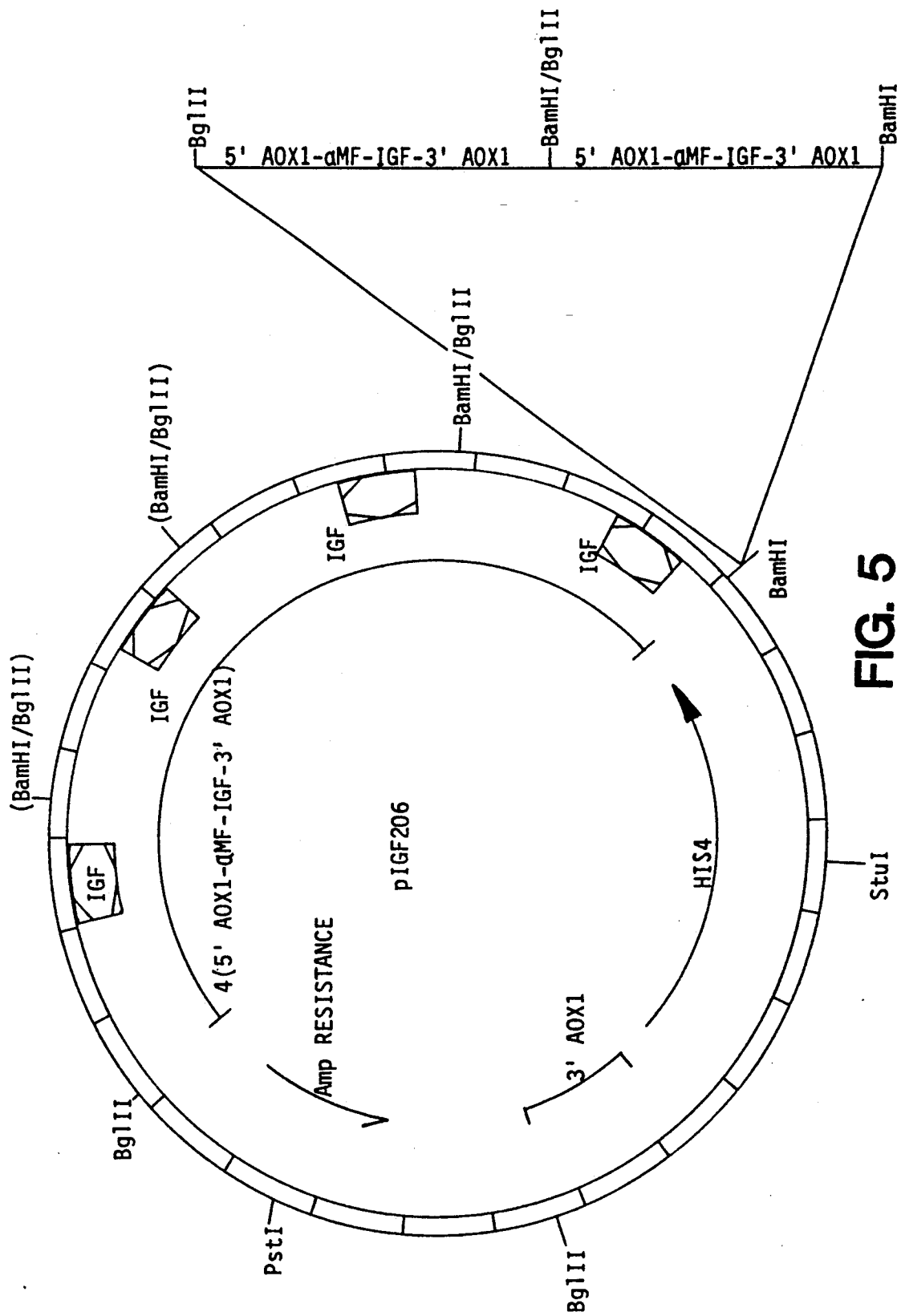
FIG. 5 is a restriction map of plasmid pIGF206.
Figure 6:
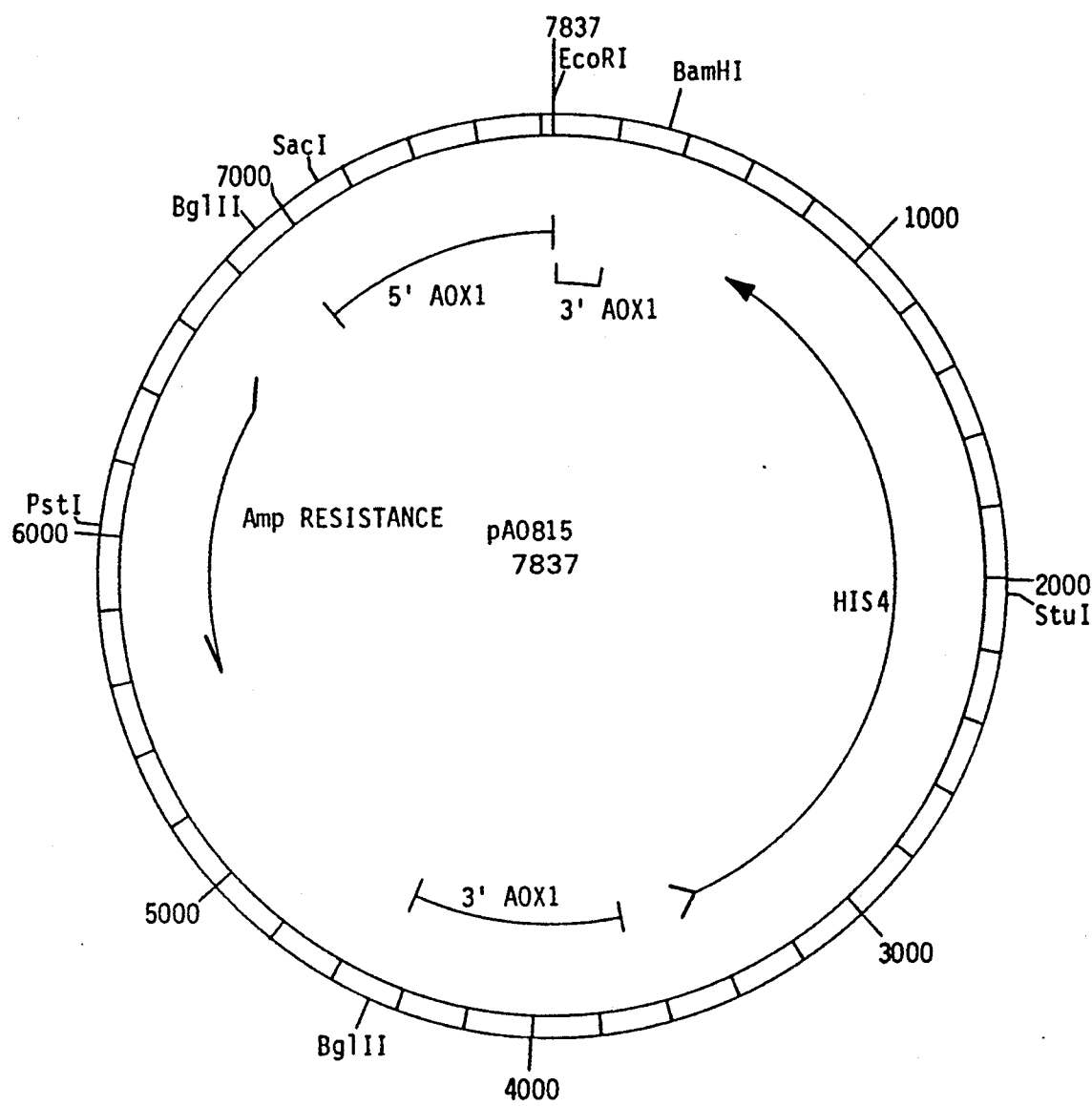
FIG. 6 is a restriction map of plasmid pAO815.

To construct expression vector pIGF206, which contains six copies of the expression cassette, the BglII-BamHI fragment from pIGF202 (250 ng) was cloned into the BamHI site of pIGF204 (10 ng; pIGF204 had been previously treated with calf alkaline phosphatase). MC1061 cells were transformed with the ligation. Amp$^R$ colonies were selected and plasmid was characterized by restriction digest. Restriction digests of the vector DNA were examined to verify the number of expression cassettes and that the expression cassettes were joined as tandem-repeat units. Correct plasmid demonstrated bands of ~6600 and 10300 bp upon digestion with ClaI and BamHI. Plasmid pIGF206 is shown in FIG. 5.

EXAMPLE 2

Development of IGF-1 expression strains a. Mut+ strains

Expression vectors pIGF201, pIGF202, pIGF204, and pIGF206 were used to develop Mut+ strains of *Pichia pastoris*. The Mut phenotype refers to the methanol utilization ability of the strain. Mut+ strains consume methanol at a rate similar to that of wild-type strains. A HIS4 mutant of *Pichia pastoris*, GS115 (ATCC 20864), was used as the host for all transformations, which were accomplished by the spheroplast method (performed as described in U.S. Pat. No. 4,879,231).

Mut+ strains were generated by integration of the entire expression vector into either the AOX1 or HIS4 locus of the host genome by an additive homologous recombination event. Plasmid pIGF201 was transformed into GS115 as an undigested circular vector and allowed to integrate randomly into the AOX1 locus at either the 5' or 3' regions homologous to sequences contained in the plasmid, or into the HIS4 locus. For site-directed addition to the HIS4 locus, the multi-copy expression vectors pIGF202, pIGF204, and pIGF206 were digested with StuI, which linearizes the plasmids within the HIS4 region. Additive integration at either the AOX1 or HIS4 locus does not disturb the AOX1 gene.

The Mut+ transformants resulting from additive integration of the expression plasmids, either randomly (pIGF201) or by site-direction (pIGF202, pIGF204, and pIGF206), were initially screened for histidine prototrophy. Prototrophic strains generated by each of the four plasmids were selected for further analysis.

Ten of the His+ is transformants resulting from transformation of GS115 with pIGF201 were analyzed by Southern blot hybridization to verify the site of integration of the expression plasmid and number of copies of the plasmid integrated. Chromosomal DNA from the 10 transformants was separately digested with EcoRI and BglII, separated by agarose gel electrophoresis, and transferred to nitrocellulose. The EcoRI digests were probed with pBR322-based plasmids containing either the AOX1 5' and 3' regions or the *Pichia pastoris* HIS4 gene. The BglII digest was probed with an oligonucleotide homologous to the IGF-1 gene.

Sixteen of the His+ transformants generated by transformation of GS115 with pIGF202, 16 generated by transformation with pIGF204, and 26 generated by transformation with pIGF206 were also analyzed by Southern blot hybridization to verify the site of integration and integrity of the multi-copy expression vector. Chromosomal DNA was digested with BglII and probed with plasmids containing the AOX1 5' and 3' regions or HIS4 gene, and also separately digested with StuI and probed with the oligonucleotide homologous to the IGF-1 coding sequence.

Analysis of DNA from ten pIGF201 transformants by Southern blot hybridization indicated that four transformants contained a single copy of the expression vector integrated at the AOX1 locus and two transformants contained multiple copies of the plasmid integrated at the HIS4 locus. The four other strains contained the plasmid integrated at unknown loci. It was not possible to determine the exact number of copies of the plasmid integrated at HIS4. Southern analysis of DNA revealed that 10 of the pIGF202 transformants, 9 of the pIGF204 transformants, and 13 of the 26 pIGF206 transformants contained a single copy of the respective expression vector integrated at HIS4. The other transformants contained plasmid integrated at unknown loci.

The following representative strains were chosen for further analysis:

| Strain Name | Plasmid Integrated | Site of Integration | Number of Plasmids Integrated | Expression Cassette Copy Number |
|---|---|---|---|---|
| G + IGF201S1 | pIGF201 | AOX1 | 1 | 1 |
| G + IGF201S2 | pIGF201 | HIS4 | Multiple | Multiple |
| G + IGF201S6 | pIGF201 | AOX1 | 1 | 1 |
| G + IGF201S10 | pIGF201 | HIS4 | Multiple | Multiple |
| G + IGF202S3 | pIGF202 | HIS4 | 1 | 2 |

| Strain Name | Plasmid Integrated | Site of Integration | Number of Plasmids Integrated | Expression Cassette Copy Number |
|---|---|---|---|---|
| G + IGF202S5 | pIGF202 | HIS4 | 1 | 2 |
| G + IGF204S2 | pIGF204 | HIS4 | 1 | 4 |
| G + IGF204S8 | pIGF204 | HIS4 | 1 | 4 |
| G + IGF206S2 | pIGF206 | HIS4 | 1 | 6 |
| G + IGF206S5 | pIGF206 | HIS4 | 1 | 6 |
| G + IGF206S8 | pIGF206 | HIS4 | 1 | 6 |
| G + IGF206S9 | pIGF206 | HIS4 | 1 | 6 |
| G + IMB202S2 | pIGF202 | HIS4 | 1 | 2 |
| G + IMB204S14 | pIGF204 | HIS4 | 1 | 4 |
| G + IMB206S1 | pIGF206 | HIS4 | 1 | 6 |
| G + IMB206S3 | pIGF206 | AOX1 | 1 | 6 | b. Mut⁻ strains

In Mut⁻ strains, the expression vector integrates into the AOX1 locus and disrupts it. Thus, Mut⁻ strains consume methanol at a much slower rate than Mut+ strains.

To generate Mut⁻ strains, plasmid pIGF206 was digested with BglII. This liberates a fragment comprised of the six IGF-1 expression cassettes, the HIS4 gene for selection, and the AOX1 3' region. Both ends of this fragment contain long sequences which are homologous to the 5' and 3' ends of the AOX1 locus. Upon transformation of GS115 hosts with the BglII-ended fragment, integration into the AOX1 locus by a homologous recombination event results in the substitution of the BglII-ended fragment for the AOX1 structural gene. Positive transformants were selected first by their His+ phenotype and then by their Mut⁻ phenotype, i.e., slow growth on methanol. This is accomplished by plating His+ transformants on minimal glucose (2%) master plates to obtain colonies originating from single cells. After overnight incubation at 30° C., the masters were replica-plated to minimal glucose plates and plates containing no carbon source to which methanol was added in vapor phase. This is accomplished by adding an aliquot, approximately 200 μl, of methanol to the underside of the top of a covered petri dish. The plates were incubated at 30° C. for 4-6 days with additional methanol added in the vapor phase every two days.

Colonies showing visible growth were scored as Mut+ and those with no visible, or slow, growth were scored as Mut⁻. Approximately 15% were slow growers, indicative of disruption of the AOX1 gene.

Following the initial screening for methanol utilization and histidine prototrophy, chromosomal DNA from three Mut⁻ transformants was analyzed by three different Southern blots to verify the site of plasmid integration and number of copies integrated.

Chromosomal DNA from Mut⁻ transformants was digested with EcoRI and probed with pBR322-based plasmids containing either the AOX5' and 3' regions or the Pichia pastoris HIS4 gene. An additional blot of BglII-digested DNA was probed with the plasmid containing the IGF-1 gene.

Southern analysis of the three Mut⁻ transformants generated using plasmid pIGF206 revealed that all three contained a single copy of the BglII fragment (comprised of six expression cassettes) integrated by replacement at the AOX1 locus.

The strains were characterized as follows:

| Strain Name | Site of Integration | Number of Plasmids Integrated | Expression cassette copy number |
|---|---|---|---|
| G-IMB206S1 | AOX1 | 1 | 6 |
| G-IMB206S2 | AOX1 | 1 | 6 |
| G-IMB206S3 | AOX1 | 1 | 6 |

EXAMPLE 3

Growth of strains in one-liter fermentations

Media employed in fermentations described herein had the following compositions:

| Chemical | Grams/liter |
|---|---|
| A. 10x BASAL SALTS | |
| Phosphoric acid, 85% | 42.0 ml |
| Calcium Sulfate.2H2O | 1.8 |
| Potassium Sulfate | 28.6 |
| Magnesium Sulfate.7H2O | 23.4 |
| Potassium Hydroxide | 6.5 |
| B. PTM₁ TRACE SALTS | |
| Cupric Sulfate.5H2O | 6.0 |
| Sodium Iodide | 0.08 |
| Manganese Sulfate.H2O | 3.0 |
| Sodium Molybdate.2H2O | 0.2 |
| Boric Acid | 0.02 |
| Cobalt Chloride | 0.5 |
| Zinc Chloride | 20.0 |
| Ferrous Sulfate.7H2O | 65.0 |
| Biotin | 0.20 |
| Sulfuric Acid | 5.0 ml | a. Mut+ protocol: methanol fed-batch fermentation i. Methanol fed-batch fermentation, pH 5 (standard Mut+ fermentation protocol) (Runs 573 and 576)

The standard Mut+ fermentation protocol includes three separate phases. Cells are grown initially on glycerol in a batch mode. Following exhaustion of the glycerol, a limited glycerol feed is initiated. During this period, glycerol does not accumulate and the AOX1 promoter is derepressed; however, cell mass increases. Finally, a methanol feed is initiated for production of heterologous protein in methanol fed-batch mode.

The fermentor is autoclaved with one liter of medium containing 500 ml of 10× basal salts medium (final basal salts concentration of 5×, see above) and 5% glycerol. After sterilization, 4 ml PTM₁ trace salts (see above) are added to the fermentor and the pH is adjusted to 5 with concentrated NH₄OH. The pH of the medium is maintained at pH 5 by addition of 50% NH₄OH containing 0.1% Struktol J673 antifoam. Inocula are prepared from buffered YNB glycerol plates and grown overnight at 30° C. in phosphate-buffered YNB (11.5 g/L $KH_2PO_4$/2.66 g/L $K_2HPO_4$/0.67% yeast nitrogen base, pH 5) containing 2% glycerol. The fermentor is inoculated with these cultured cells to an $OD_{600}$ of 1–6, and the batch growth regimen is continued for 18 to 24 hours. At the point of glycerol exhaustion, indicated by increased dissolved oxygen, a glycerol feed (50% glycerol plus 12 ml/L of $PTM_1$) is initiated at a rate in the range of about 5–20 mL/h. This period of growth on limited glycerol is continued until a total volume of approximately 100 mL of feed is added to the fermentor. After addition of 100 mL of the glycerol feed, a methanol feed (100% methanol plus 12 ml/L $PTM_1$) is started. The initial rate of methanol addition is approximately 1–2 mL/h. The methanol feed rate is increased in increments of 10% every 30 minutes over the course of 8 hours until a final feed rate of 5–6 mL/h is attained. The vessel is harvested 48–80 hours following methanol induction.

ii. Extended glycerol feed, methanol fed-batch fermentation, pH 5 (Run 694), and pH adjustment from 5 to 3.5 (Run 578)

To increase the wet cell weight level at the time of methanol addition, a modified fermentation protocol was used for Run 694 in which the limited glycerol feed was increased so as to provide a total volume of approximately 200 mL of glycerol-containing feed to the fermentor prior to methanol induction. Run 694 was then harvested 94 hours after methanol induction.

In addition, to investigate the possibility that proteolytic degradation of recombinant IGF-1 might be occurring in the broth, the pH of the fermentor was adjusted in Run 578 from the standard pH of 5 to a pH of 3.5 by the addition of 85% phosphoric acid after 26 hours of growth on methanol. The fermentor was then harvested after 75 hours of growth at pH 3.5 (101 hours of growth in the presence of methanol).

iii. Extended glycerol feed, methanol fed-batch fermentations, low pH (Runs 596, 598, 599, 605, 606, 613, 661, 679, 680, 691, 698 and 699)

Additional fermentations were conducted with an extended glycerol feed (i.e., to provide a total volume of approximately 200 mL of glycerol-containing feed to the fermentor prior to methanol induction) at low pH. Runs 596, 605, 606, and 613 were conducted at pH 3, while Run 598 was conducted at pH 3.5. In Run 599, cells were grown in glycerol fed-batch and limited glycerol phases at pH 3.5. At the start of the third phase, when the methanol feed was initiated, the pH controller was set at 3, and the pH was slowly adjusted over a period of one to two hours. All of these fermentation runs were harvested after 48 to 64 hours on methanol.

In runs 657, 661, 679, 680, 691, 698, and 699, the pH was started at 5 during the glycerol batch phase. During the glycerol fed-batch phase, the pH control set point was adjusted to 3.0 so that the pH fell to 3 as a result of cellular metabolism. The runs were then harvested 73–101 hours after methanol induction.

iv. Extended glycerol feed, methanol fed-batch fermentations, pH 3 (Runs 705 and 706)

In additional extended glycerol feed, low pH fermentations, the time period over which the glycerol feed was introduced was increased so as to provide a total volume of approximately 300 mL of glycerol-containing feed to the fermentor prior to methanol induction. In these runs, the pH controller was adjusted to allow the pH to decrease to 3 as a result of cellular metabolism. The pH was then maintained at 3 for the remainder of the run. A methanol feed (100% methanol plus 12 ml/l $PTM_1$) was initiated after termination of the glycerol feed. The initial rate of methanol addition was approximately 2 mL/hr. After three hours, the methanol feed rate was increased to 6 mL/hr and maintained at that rate throughout the remainder of each run. The vessel was then harvested about 41–43 hours after the introduction of methanol to the medium.

v. Extended glycerol feed, methanol fed-batch fermentation, pH 2.9 (Run 756)

This fermentation was conducted as described in (iv) above, except 240 mL glycerol (instead of 300 mL) were added during the glycerol fed-batch phase. The run was stopped after 72 hours on methanol.

vi. Reduced glycerol feed, methanol fed-batch fermentations, pH 2.9 or 2.7 (Runs 755, 775, 776)

To decrease the cell density which accumulated during the glycerol growth phases, the glycerol batch phase was reduced from 5% (w/v) to 2% (w/v) glycerol, and the glycerol fed-batch phase was reduced to 40 mL of a 50% (w/v) glycerol feed. An additional change in the fermentation protocol was to reduce the pH controller set point to 2.7 (Runs 775 and 776) or 2.9 (Run 755) during the glycerol fed-batch phase. The methanol feed was initiated at 2 mL/hr, then increased to 6 mL/hr after 3 hr. The fermentations were then harvested after 70–72 hr on methanol.

Mut$^-$ protocol methanol fed-batch fermentation (Run 657)

The first two phases of the methanol fed-batch fermentations of the Mut$^-$ strains were conducted as described for the Mut$^+$ strain fermentations in Example 3(a)(iii). However, the methanol induction phases of the Mut$^+$ and Mut$^-$ fermentation protocols differed in terms of the manner in which the methanol feeds were added to the cultures. In standard fermentations of the Mut$^-$ strain, the methanol feed rate was adjusted to maintain an excess of methanol in the medium which did not exceed 0.3% (as determined by gas chromatography). The methanol feed was initiated at 1 mL/hr and after two hours was increased in 10% increments every 30 minutes to a rate of 3 mL/hr which was maintained for the duration of the fermentation. The vessel was then harvested after 101 hours of growth of the strain on methanol.

c. Results

The expression data are summarized in the following Table:

| Run Number (Strain) | Expression Cassette Copy Number | pH | Hours on Methanol | Cell Density (g/l) | IGF-1 (mg/L) |
| --- | --- | --- | --- | --- | --- |
| 573 (G + IGF201S1) | 1 | 5 | 49 | 308 | 11[b] |
| 576 (G + IGF206S2) | 6 | 5 | 49 | 280 | 117[b] |
| 578 (G + IGF206S2) | 6 | 3.5 | 101[c] | 360 | 284[b] |
| 596 (G + IGF206S2) | 6 | 3 | 48 | 385 | 1850[a]/555[b] |
| 598 (G + IGF206S2) | 6 | 3 | 64 | 363 | 455[b] |
| 599 (G + IGF206S2) | 6 | 3 | 64 | 245 | 354[b] |
| 605 (G + IGF201S1) | 1 | 3 | 64 | 415 | 167[a]/21[b] |
| 606 (G + IGF206S2) | 6 | 3 | 64 | 311 | 463[b] |
| 613 (G + IGF206S2) | 6 | 3 | 495 | 344 | 489[b] |
| 657 (G − IMB206S3) | 6 | 3 | 101 | 370 | 745[a] |
| 661 (G + IMB206S1) | 6 | 3 | 73 | 320 | 1280[a]/140[d] |
| 679 (G + IMB206S1) | 6 | 3 | 73 | 375 | 1630[a]/110[d] |
| 680 (G + IMB202S2) | 2 | 3 | 73 | 430 | 740[a]/64[d] |
| 691 (G + IMB204S14) | 4 | 3 | 92 | 350 | 1400[a]/174[d] |
| 694 (G + IMB206S1) | 6 | 5 | 94 | 325 | 306[a]/15[d] |
| 698 (G + IMB206S1) | 6 | 3 | 73 | 330 | 1185[a] |
| 699 (G + IMB206S1) | 6 | 3 | 73 | 315 | 1170[a] |
| 705 (G + IMB206S1) | 6 | 3 | 43 | 335 | 930[a]/90[d] |
| 706 (G + IMB204S14) | 4 | 3 | 41 | 370 | 700[a]/100[d] |
| 755 (G + IMB204S14) | 4 | 2.9 | 72 | 459 | 300[d] |
| 756 (G + IMB204S14) | 4 | 2.9 | 72 | 445 | 315[d] |
| 775 (G + IMB204S14) | 4 | 2.7 | 71 | 420 | 280[d] |
| 776 (G + IMB206S1) | 6 | 2.7 | 71 | 490 | 355[d] |

[a] RIA [determined as described in Example 4(a)]
[b] average from three Western blots
[c] 26 hr at pH 5, 75 hr at pH 3.5
[d] RIA [Nichols; see Example 4(a)]

From these data it is clear that immunoreactive IGF-1 is secreted from *P. pastoris* cells transformed with expression vectors pIGF201, pIGF202, pIGF204, and pIGF206. Second, an effect of expression cassette copy number is seen in the level of immunoreactive IGF-1 measured in the media. Compare the expression level of IGF-1 measured by RIA [see Example 4(a)] from one copy (Run 605; 167 mg/L), two copy (Run 680; 740 mg/L), four copy (Run 691; 1400 mg/L), and six copy strains (Run 596; 1850 mg/L). Third, the Mut+ six copy strains (see, for example, Runs 698 and 699) appeared superior to the Mut− six copy strain (Run 657). Fourth, the level of IGF-1 product determined by Nichols RIA [see Example 4(a)] was significantly higher in fermentations conducted at lower pHs: compare Run 694 (pH 5; 15 mg/L) to Run 661 (pH 3; 140 mg/L), and Run 776 (pH 2.7; 355 mg/L). Fifth, decreasing the cell density which accumulates in the glycerol phase had little effect on the final cell density or final IGF-1 concentration.

EXAMPLE 4

Characterization of IGF-1 a. Assay - RIA

A 1:5000 final dilution of rabbit anti-human IGF-1 antisera (Incstar anti-somatomedin C antibody, catalog #22275), 10,000–12,000 cpm of $^{125}$I-IGF-1 (Incstar catalog #22303), and various dilutions of recombinant human IGF-1 standard (purchased from Imcera and quantitated by amino acid analysis) or the unknown broth solution were incubated overnight at 4° C. in a final volume of 0.5 ml in 12×75 mm polystyrene tubes. At the end of the incubation, 100 μl of Pansorbin (working dilution of 1:40) was added to the tubes and incubated for 15 minutes at room temperature. Two milliliters of RIA buffer (50 mM NaPO$_4$, 0.1% BSA, 0.1% NaN$_3$, and 0.1% Triton X-100, pH 7.4) were added to each tube before centrifugation at 3200 rpm for 68 minutes at 4° C. in a Beckman J6M centrifuge. Following centrifugation, the supernatant was decanted and the radioactivity associated with the pelleted material was determined in a gamma counter.

Alternatively, some of the samples were assayed using a commercial RIA offered by Nichols (Nichols Institute Diagnostic; San Juan Capistrano, Calif.). The Nichols assay consistently measured lower levels of IGF-1 than the RIA described above (see data above for Runs 661, 679, 680, 691, 694, 705, and 706). The discrepancy is most likely due to the ability of the antibody in the RIA described above to measure monomer and multimer, whereas the antibody used in the Nichols assay measures monomer only.

b. Western blot i. Procedure

Samples of cell-free broth obtained at the conclusion of selected fermentations of the Mut+ and Mut− IGF-1-expressing strains of *Pichia pastoris* were analyzed by Tricine SDS-PAGE and western blots. The proteins were first separated by electrophoresis and then transferred to 0.1 μm nitrocellulose by electroblot in a solution of Towbin buffer (25 mM Tris-HCl, pH 8.3, 190 mM glycine, 20% methanol) for at least 90 minutes at 20 V/cm. After the proteins were transferred onto nitrocellulose, the filter was incubated for one hour in blocking buffer (0.25% gelatin, phosphate-buffered saline, 0.05% Tween 20, 0.02% sodium azide). Rabbit anti-IGF-1 antisera 10A was diluted 1:2000 with blocking buffer and incubated with the filter for a minimum of two hours. Antibody 10A was raised against a synthetic peptide corresponding to the last 14 amino acids of the carboxy terminus of human IGF-1, which was conjugated to human α-globulin. The antisera was adsorbed to α-globulin prior to use. The filter was washed with blocking buffer for an hour and incubated with $^{125}$I-Protein A (0.02 μCi/ml) for 45 minutes. After one hour of washing with blocking buffer, the filter was air dried and exposed to X-ray film with an intensifying screen at −75° C.

ii. Results

Several characteristics of Mut+ *Pichia pastoris*-produced IGF-1 were ascertained from Western analysis. First, if the broth samples were not reduced prior to electrophoresis, the IGF-1 migrated as several forms which appeared to be a monomer, dimer and various multimers of IGF-1. The ratio or profile of monomer to multimer forms of secreted IGF-1 did not seem to be affected by copy number. Second, the Western blot of reducing gels revealed the absence of most of the higher molecular weight immunoreactive species that were evident in the nonreduced broth samples, and revealed the presence of a protein that co-migrates with IGF-1 standard (monomer) as well as an immunoreactive protein which migrates to a position slightly below that of standard IGF-1. N-terminal protein sequence analysis (Example 4.e.) of this lower molecular weight immunoreactive species demonstrated that it begins with residue 25 of mature human IGF-1 and, thus, is a proteolytic fragment of IGF-1. However, since this band is not seen under non-reducing conditions, the IGF-1 molecule may be only nicked between residues 24 and 25, i.e., not completely fragmented, with the disulfide bonds at Cys-6/Cys-48 and Cys-18/Cys-61 of IGF-1 holding the peptide fragments consisting of amino acids 1–24 and 25–70 together. The level of this "nicked" peptide was decreased to zero in modified run 705 (using the six-copy strain G+IMB206S1), and was higher in modified run 706 (using the four-copy strain G+IMB204S14). Further, the decreased glycerol fermentation (Run 755) produced wholly intact IGF-1 molecules (no degradation), while the extended glycerol feed fermentation (Run 756) demonstrated a low level of degraded product. The degradation appeared to be slightly higher with the six-copy strain (Run 776) than with the four-copy strain (Run 775).

IGF-1 produced in the fermentation of the six-copy Mut− strain (Run 657) was also analyzed by SDS-PAGE and Western blot. The IGF-1 band patterns of reduced and non-reduced broth from the fermentation of the six-copy Mut− strain are similar to the band patterns of reduced and non-reduced broth from the fermentations of the six-copy and four-copy Mut+ strains.

c. Radioreceptor assay (RRA).

i. Protocol

A radioreceptor assay (RRA) for evaluating the bioactivity of *Pichia pastoris*-produced IGF-1 was carried out at the Indiana University School of Medicine with freshly prepared human placental membranes. Standard curves were generated with receptor grade IGF-1 from Imcera at concentrations ranging from 0.075 to 300 ng/mL. Unknown samples and IGF-1 standard were diluted in 0.05 M Tris, pH 7.4, containing 2.5 g/L bovine serum albumin. An appropriate amount of placental membrane preparation and $^{125}$I-IGF-1 (12,500 cpm) were added to the diluted samples. The mixture was incubated at 4° C. for 16–20 hours in a final volume of 0.5 ml. The tubes were then centrifuged at 6000× g for 30 minutes. The supernatant was removed and the pellets were washed in assay buffer. The radioactivity associated with the pellets was measured in a gamma counter and unknown concentrations were determined by comparing the counts bound to the pellet to the counts bound in the presence of known amounts of standard as depicted in the standard curve. An $ED_{50}$ of approximately 2–3 ng/ml was calculated from the standard curve. Non-specific binding was 400 cpm.

ii. Results

Crude broth samples were found to have low values for IGF-1 receptor binding. However, analysis of IGF-1 partially purified from fermentation broth revealed that at least 50% of the RIA-active material was also active in the RRA.

d. Partial purification i. Ultrafiltration

Partial purification of IGF-1 secreted by recombinant strains of *Pichia pastoris* during growth in one-liter fermentations was achieved by ultrafiltration of cell-free fermentation broth in an Amicon pressure cell using YM filters of various sizes. Cell-free broth was obtained by centrifugation of fermentor culture samples at 6500× g for 30 minutes. The cell-free broth was then filtered through a 0.45 μm pore size filter unit (Corning) to remove any remaining debris. Following this filtration step, the cell-free broth was loaded into two 400-ml Amicon pressure cells containing YM10 filters with a molecular-weight-cut-off of 10,000. Each pressure cell was continually diluted with 30 mM potassium phosphate buffer, pH 3, while maintaining a constant volume in the pressure cell. The buffer reservoirs were pressurized to 60 psi and buffer was continually fed into the ultrafiltration pressure cells.

The filtrates from each of the two pressure cells were pooled together as Pool #1. A second filtrate pool was prepared by pooling the filtrates obtained after feeding additional buffer into the two pressure cells and continuing the ultrafiltration process.

In order to reduce the volume of the partially purified IGF-1, the two filtrate pools were filtered through YM5 filters with a molecular-weight-cut-off of 5000. Pool #1 was loaded into two 400-ml pressure cells containing YM5 filters. Pool #2 was then fed into the two pressure cells from two 5-liter reservoirs (pressurized to 60 psi), each of which contained 2.1 liters of Pool #2. Filtration of the two filtrate pools was conducted in this manner because the majority of the color and contaminants were present in Pool #1. Therefore, using the colorless Pool #2 as a "wash solution" to filter the Pool #1 material that was loaded into the pressure cells served to wash the color-containing substance through the 5K-cut-off filters while the IGF-1 of both Pool #1 and #2 was being concentrated in the pressure cells. After substantial reduction of the volume of the partially purified IGF-1, the concentrated material was further washed by adding 30 mM potassium phosphate buffer, pH 3, to the reservoir. The volume of the partially purified IGF-1 was further reduced by this wash and the final sample of concentrated product was divided into aliquots and stored frozen at −70° C.

ii. Reverse phase HPLC analysis

A Waters 600 solvent delivery system, Waters Model 481 Lamba Max variable wavelength detector, Wisp 710B auto-injector and a Shimadzu Chrom-Pac integrator constituted the HPLC system utilized in the analysis of *Pichia pastoris*-produced IGF-1. A Vydac C4 column (0.1×5 cm) with a guard column was used to separate broth components in a trifluoroacetic acid (TFA)-/acetonitrile gradient. Mobile phase A (0.1% TFA) was used to dilute mobile phase B (95% acetonitrile/5% water with 0.1% TFA). Samples were diluted in 20% mobile phase B before being loaded onto the column. Broth components were eluted from the column in a 15-minute linear 25–55% gradient of mobile phase B. The column was regenerated by addition of a 5-minute 100% mobile phase B wash followed by equilibration in 25% mobile phase B for 10 minutes.

e. Protein sequencing i. Protocol

The N-terminal amino acid sequence of protein partially purified from cell-free broth samples by reverse phase HPLC and by ultrafiltration was determined using an Applied Biosystems 470/120 Gas Phase Protein Sequencer according to the methods described by Hunkapiller and Hood [*Science* 219: 650 (1983) and Hewick et al. [*J. Biol. Chem.* 256: 7990 (1981)].

In order to characterize the proteins that appeared as prominent bands on Coomassie-stained gels (reduced and non-reduced) of cell-free broth, the samples were electroblotted from the gel onto Immobilon (Millipore), stained and destained. The bands corresponding to the predominant protein species were excised from the Immobilon strip and used in the determination of the N-terminal amino acid sequence of the protein according to the method described by Matsudaira [*J. Biol. Chem.* 262: 10035 (1987)]. Briefly, the procedure involved the following steps. First, the gel was soaked for five minutes in 10 mM CAPS buffer (10 mM 3-[cyclohexylamino]-1-propanesulfonic acid/10% methanol, pH 11.0). A polyvinylidene difluoride (PVDF) Immobilon membrane was pre-wetted in a small volume of 100% methanol for one-to-two seconds and then soaked in the CAPS transfer buffer. The blotting cassette (Bio-Rad Miniblotter) was assembled in the normal fashion with the PVDF membrane adjacent to the gel. The protein was transferred onto the membrane at 200 mA for 60 minutes. Following transfer, the membrane was stained in Coomassie Blue (0.1% Coomassie Blue R-250, 50% methanol) for 5 minutes followed by rapid destaining for 5–10 minutes in 50% methanol, 10% acetic acid. The areas of the Immobilon corresponding to IGF-1 were excised and loaded into the protein sequencer.

ii. Results

The final concentrated sample of partially purified material from Run 706 was subjected to protein sequence analysis. Two sequences were identified. The N-terminus of the first sequence consisted of amino acids A-P-V from the AMF pre-pro peptide. The N-terminal amino acid sequence of the remainder of the sample, G-P-E-T-L, corresponds to the N-terminus of authentic human IGF-1.

EXAMPLE 5

Construction of plasmid pAO203

The AOX1 transcription terminator was isolated from 20 μg of [pPG2.0=BamHI-HindIII fragment of pG4.0 (NRRL 15868)+pBR322] by StuI digestion followed by the addition of 0.2 μg SalI linkers (GGTCGACC). The plasmid was subsequently digested with HindIII and the 350 bp fragment isolated from a 10% acrylamide gel and subcloned into pUC18 (Boehringer Mannheim) digested with HindIII and SalI. The ligation mix was transformed into JM103 cells (that are widely available) and $Amp^R$ colonies were selected. The correct construction was verified by HindIII and SalI digestion, which yielded a 350 bp fragment, and was called pAO201.

5 μg of pAO201 was digested with HindIII, filled in using *E. coli* DNA Polymerase I Klenow fragment, and 0.1 μg of BglII linkers (GAGATCTC) were added. After digestion of the excess BglII linkers, the plasmid was reclosed and transformed into MC1061 cells. $Amp^R$ cells were selected, DNA was prepared, and the correct plasmid was verified by BglII, SalI double digests, yielding a 350 bp fragment, and by a HindIII digest to show loss of HindIII site. This plasmid was called pAO202.

An alpha factor-GRF fusion was isolated as a 360 bp BamHI-PstI partial digest from pYSV201. Plasmid pYSV201 is the EcoRI-BamHI fragment of GRF-E-3 inserted into M13mp18 (New England Biolabs). Plasmid GRF-E-3 may be constructed by cloning DNA encoding the alpha factor pre-pro sequence and linking it to DNA encoding GRF.

Alpha-factor genomic DNA was cloned by screening a genomic DNA library of Sau3A partially digested *Saccharomyces cerevisiae* DNA inserted in the BamHI site of YEp13, which was obtained from the ATCC under accession number 37115. The DNA for the library was prepared from *Saccharomyces cerevisiae* strain AB320 (HO, ade2-1, lys2-1, trp5-2, leu2-1, can1-100, ura3-1, ura1-1, met4-1), partially digested and inserted into YEp13. *E. coli* was transformed with the library using competent MC1061 cells and a heat shock step. The cells were rendered competent by growing to mid-log ($OD_{600}$=0.3), incubating in $CaCl_2$, at half the original volume, for 30 minutes on ice, centrifuging, and resuspending the cells in 1/50 of the original volume of 10% glycerol in 50 mM $CaCl_2$. The cells were then quick frozen and stored at −70° C. For transformation, the 100 μl of cells were thawed on ice and added to 10 ng of the DNA and incubated on ice for 15 minutes. The cells were then placed at 37° C. for 5 minutes, followed by a 23° C. incubation. The cells were spread onto 1.5% agar plants containing L-broth and 50 μg/ml of ampicillin for selection of ampicillin resistant transformants. About $10^4$ ampicillin-resistant transformants were obtained from the YEp13 library.

The resistant colonies were plated onto five plates at a density of 4000 colonies per plate. Duplicate colony hybridization filters were prepared and probed with a $^{32}P$ labeled probe having the sequence CGCAGCATTCTTCGCATTAGC. Prehybridization was performed at 42° C. in 6xSSPE (1xSSPE is 0.18M NaCl, 10 MM $NaPO_4$, PH 7.0, 1 mM EDTA), 10× Denhardt's (1× denhardt's is 0.02% bovine serum albumin, 0.02% Ficoll, 0.02% polyvinylpyrollidone), 0.5% SDS for 3 hours. Hybridization was performed as above, but with 10% dextran sulfate and $10^6$ cpm of probe per ml of hybridization buffer at 42° C. for 18 hours. The filters were washed with 2xSSC and 0.5% SDS at room temperature. Seven positive colonies were identified.

Colonies showing strong hybridization with the probe in duplicate were isolated, further purified, and rehybridized with the 21 base oligomer as described. Four positive colonies were isolated. DNA was prepared from 1.5 ml cultures of the positive colonies and analyzed by restriction enzyme digestion. DNA from two of the colonies included a 1.7 kb EcoRI fragment containing the alpha gene promoter, structural gene and transcription terminator. Southern analysis confirmed that this fragment hybridized to the 21 base oligomer.

Sequencing of the insert confirmed that the isolated DNA had the correct sequence and encoded the alpha factor gene.

One of the selected clones was digested with EcoRI and HindIII and the 1200 bp EcoRI-HindIII fragment was isolated and ligated into pBR322 that had been digested with EcoRI and HindIII. The resulting plasmid was designated p-alpha-factor.

DNA encoding human pancreatic GRF (hGRF) designed for expression in *E. coli* (including DNA encoding 44 amino acids and an artificial initiator methionine) was obtained as a chemically synthesized EcoRI-BamHI fragment and was purchased from Creative Biomolecules. The synthetic fragment had the following sequence:

| Met | Tyr | Ala | Asp | Ala | Ile | Phe | Thr | Asn | Ser | Tyr | Arg | Lys | Val | Leu |
|---|---|---|---|---|---|---|---|---|---|---|---|---|---|---|
| ATG | TAC | GCA | GAC | GCT | ATC | TTT | ACT | AAC | TCT | TAC | CGT | AAA | GTT | CTG |
| 1 | 2 | 3 | 4 | 5 | 6 | 7 | 8 | 9 | 10 | 11 | 12 | 13 | 14 |

| Gly | Gln | Leu | Ser | Ala | Arg | Lys | Leu | Leu | Gln | Asp | Ile | Met | Ser | Arg |
|---|---|---|---|---|---|---|---|---|---|---|---|---|---|---|
| GGC | CAG | CTG | TCT | CGA | CGC | AAG | CTT | CTG | CAG | GAT | ATC | ATG | TCT | AGA |
| 15 | 16 | 17 | 18 | 19 | 20 | 21 | 22 | 23 | 24 | 25 | 26 | 27 | 28 | 29 |

| Gln | Gln | Gly | Glu | Ser | Asn | Gln | Glu | Arg | Gly | Ala | Arg | Ala | Arg |
|---|---|---|---|---|---|---|---|---|---|---|---|---|---|
| CAG | CAG | GGC | GAA | TCT | AAC | CAG | GAG | CGT | GGC | GCC | CGT | GCA | CGC |
| 30 | 31 | 32 | 33 | 34 | 35 | 36 | 37 | 38 | 39 | 40 | 41 | 42 | 43 |

| Leu | Stop |
|---|---|
| CTG | TAG. |
| 44 | |

DNA encoding an EcoRI site was linked to the 5' end of the fragment and DNA encoding a BamHI site was linked to the 3' end and includes the G from the stop codon.

The ATG encoding Met$^{27}$ was changed to CTG encoding Leu$^{27}$ to produce GRFD' (Leu$^{27}$-hgrf(1-44)-OH). This was accomplished by ligating the above fragment into pBR322 and digesting with HindIII and XbaI. Changing the Met codon to a Leu codon using an oligonucleotide having the sequence:

```
5'  AGCTCCTGCAGGATATCCTGT 3'
3'       GGACGTCCTATAGGACAGATC 5'
``` also eliminated a HindIII site at the DNA encoding amino acids 21 and 22. To effect these changes the oligonucleotide was ligated with the XbaI/HindIII-cut vector and the resulting mixture was transformed into MC1061. Transformants were screened for the presence of two PvuII sites. In order to eliminate plasmids with multiple inserts, the selected plasmids were digested with XbaI and religated at a concentration of 20 ng/μl. MC1061 cells were transformed with the resulting mixture and ampicillin-resistant colonies were selected and analyzed by digestion with EcoRI and BamHI. Plasmids containing 140 bp fragments, instead of 190 bp fragments, were designated GRF-D'.

GRF-D' was digested with HgaI and BamHI and a 118 bp fragment was isolated and ligated with the following oligonucleotide that replaces the amino acids eliminated by HgaI digestion, removes the n-terminal Met, and leaves a 5' overhang that can ligate with the HindIII end of the pre-pro-alpha factor encoding DNA:

```
5'  AGCTTACGCAGACGCTATCT 3'
3'      ATGCGTCTGCGATAGAAATGA 5'.
```

The ligated insert was digested with BamHI and HindIII in order to eliminate multimers and was then ligated to HindIII-BamHI-digested plasmid p-alpha factor. The resulting mixture was transformed into MC1061 cells and ampicillin-resistant transformants selected. Plasmid from a selected transformant that contained the correct insert was designated GRF-E-3. Thus, GRF-E-3 contains the 5'-upstream region of the gene encoding alpha-factor from the EcoRI site to the initiation codon and the DNA encoding the complete pre-pro-alpha-factor leader. The GRF encoding DNA is linked such that the DNA encoding the first amino acid of GRF (gly) immediately follows the processing sites for alpha-factor. Thus, the insert encodes the fusion protein having the formula: alpha factor leader peptide—lys—arg—glu—ala—glu—ala—hGRF—OH.
(processing site)

Twenty μg of pYSV201 plasmid was digested with BamHI and partially digested with PstI. To this partial digest was added the following oligonucleotides:

```
5'  AATTCGATGAGATTTCCTTCAATTTTTACTGCA 3'
3'      GCTACTCTAAAGGAAGTTAAAAATG 5'.
```

Only the antisense strand of the oligonucleotide was kinase labelled so that the oligonucleotides did not polymerize at the 5'- end. After acrylamide gel electrophoresis (10%), the fragment of 385 bp was isolated by electroelution. This EcoRI- BamHI fragment of 385 bp was cloned into pAO202 which had been cut with EcoRI and BamHI. Routinely, 5 ng of vector cut with the appropriate enzymes and treated with calf intestine alkaline phosphatase, was ligated with 50 ng of the insert fragment. MC1061 cells were transformed, Amp$^r$cells were selected, and DNA was prepared. The resulting plasmid, pAO203, was identified by cutting with EcoRI and BglII to yield a fragment of greater than 700 bp.

EXAMPLE 6

Construction of plasmid pAO815

Plasmid pAO815 was constructed by mutagenizing plasmid pAO807 (which was in turn prepared as described hereinbelow) to change the ClaI site downstream of the AOX1 transcription terminator in pAO807 to a BamHI site. The oligonucleotide used for mutagenizing pAO807 had the following sequence:

5'-GAC GTT CGT TTG TGC GGA TCC AAT
GCG GTA GTT TAT-3'.

The mutagenized plasmid was called pAO807-Bam. Plasmid pAO804 (described in WO 89/04320) was digested with BglII and 25 ng of the 2400 bp fragment were ligated to 250 ng of the 5400 bp BglII fragment from BglII-digested pAO807-Bam. The ligation mix was transformed into MC1061 cells and the correct construct was verified by digestion with PstI/BamHI to identify 6100 and 2100 bp sized bands. The correct construct was called pAO815. The restriction map of the expression vector pAO815 is shown in FIG. 7.

Construction of plasmid pAO807

1. Preparation of fl-ori DNA fl bacteriophage DNA (50 μg) was digested with 50 units of RsaI and DraI (according to manufacturer's directions) to release the ≈458 bp DNA fragment containing the fl origin of replication (ori). The digestion mixture was extracted with an equal volume of phenol:chloroform (V/V) followed by extracting the aqueous layer with an equal volume of chloroform and finally the DNA in the aqueous phase was precipitated by adjusting the NaCl concentration to 0.2M and adding 2.5 volumes of absolute ethanol. The mixture was allowed to stand on ice (4° C.) for 10 minutes and the DNA precipitate was collected by centrifugation for 30 minutes at 10,000× g in a microfuge at 4° C.

The DNA pellet was washed 2 times with 70% aqueous ethanol. The washed pellet was vacuum dried and dissolved in 25 μl of TE buffer [1.0 mM EDTA in 0.01M (pH 7.4) Tris buffer]. This DNA was electrophoresed on 1.5% agarose gel and the gel portion containing the ≈458 bp fl-ori fragment was excised out and the DNA in the gel was electroeluted onto DE81 (Whatman) paper and eluted from the paper in 1M NaCl. The DNA solution was precipitated as detailed above and the DNA precipitate was dissolved in 25 μl of TE buffer (fl-ori fragment).

2. Cloning of fl-ori into Dra I sites of pBR322 pBR322 (2 μg) was partially digested with 2 units DraI (according to manufacturer's instructions). The reaction was terminated by phenol:chloroform extraction followed by precipitation of DNA as detailed in step 1 above. The DNA pellet was dissolved in 20 μl of TE buffer. About 100 ng of this DNA was ligated with 100 ng of fl-ori fragment (step 1) in 20 μl of ligation buffer by incubating at 14° C. for overnight with 1 unit of T4 DNA ligase. The ligation was terminated by heating to 70° C. for 10 minutes and then used to transform E. coli strain JM103 [Janisch-Perron et al., Gene, vol 22, 103(1983)]. Amp$^R$ transformants were pooled and superinfected with helper phage R408 [Russel et al., supra]. Single stranded phage were isolated from the media and used to reinfect JM103. Amp$^R$ transformants contained pBRfl-ori which contains fl-ori cloned into the Dra I sites (nucleotide positions 3232 and 3251) of pBR322.

3. Construction of plasmid pAO807 pBRfl-ori (10 μg) was digested for 4 hours at 37° C. with 10 units each of Pst I and Nde I. The digested DNA was phenol:chloroform extracted, precipitated and dissolved in 25 μl of TE buffer as detailed in step 1 above This material was electrophoresed on a 12% agarose gel and the Nde I - Pst I fragment (approximately 0.8 kb) containing the fl-ori was isolated and dissolved in 20 μl of TE buffer as detailed in step 1 above. About 100 ng of this DNA was mixed with 100 ng of pAO804 (which was in turn prepared as described hereinbelow) that had been digested with Pst I and Nde I and phosphatase-treated. This mixture was ligated in 20 μl of ligation buffer by incubating overnight at 14° C. with 1 unit of T4 DNA ligase. The ligation reaction was terminated by heating at 70° C. for 10 minutes. This DNA was used to transform E. coli strain JM103 to obtain pAO807.

Construction of plasmid pAO804

Plasmid pAO804 has been described in PCT Application No. WO 89/04320. Construction of this plasmid involved the following steps:

Plasmid pBR322 was modified as follows to eliminate the EcoRI site and insert a BglII site into the PvuII site:

pBR322 was digested with EcoRI, the protruding ends were filled in with Klenow Fragment of E. coli DNA polymerase I, and the resulting DNA was recircularized using T4 ligase. The recircularized DNA was used to transform E. coli MC1061 to ampicillin-resistance and transformants were screened for having a plasmid of about 4.37 kbp in size without an EcoRI site. One such transformant was selected and cultured to yield a plasmid, designated pBR322ΔRI, which is pBR322 with the EcoRI site replaced with the sequence:

5'-GAATTAATTC-3'

3'-CTTAATTAAG-5'.

pBR322ΔRI was digested with PvuII, and the linker having the sequence:

5'-CAGATCTG-3'

3'-GTCTAGAC-5' was ligated to the resulting blunt ends employing T4 ligase. The resulting DNAs were recircularized, also with T4 ligase, and then digested with BglII and again recircularized using T4 ligase to eliminate multiple BglII sites due to ligation of more than one linker to the PvuII-cleaved pBR322ΔRI. The DNAs, treated to eliminate multiple BglII sites, were used to transform E. coli MC1061 to ampicillin-resistance. Transformants were screened for a plasmid of about 4.38 kbp with a BglII site. One such transformant was selected and cultured to yield a plasmid, designated pBR322ΔRIBGL, for further work. Plasmid pBR322ΔRIBGL is the same as pBR322ΔRI except that pBR322ΔRIBGL has the sequence

5'-CAGCAGATCTGCTG-3'

3'-GTCGTCTAGACGAC-5' in place of the PvuII site in pBR322ΔRI.

pBR322ΔRIBGL was digested with a SalI and BglII and the large fragment (approximately 2.97 kbp) was isolated. Plasmid pBSAGI5I, which is described in European Patent Application Publication No. 0 226 752,was digested completely with BglII and XhoI and an approximately 850 bp fragment from a region of the P. pastoris AOX1 locus downstream from the AOX1 gene transcription terminator (relative to the direction of transcription from the AOX1 promoter) was isolated. The BglII-XhoI fragment from pBSAGI5I and the approximately 2.97 kbp, SalI-BglII fragment from pBR322ΔRIBGL were combined and subjected to ligation with T4 ligase. The ligation mixture was used to transform E. coli MC1061 to ampicillin-resistance and transformants were screened for a plasmid of the expected size (approximately 3.8 kbp) with a BglII site. This plasmid was designated pAO801. The overhanging end of the SalI site from the pBR322ΔRIBGL fragment was ligated to the overhanging end of the XhoI site on the 850 bp pBSAGI5I fragment and, in the process, both the SalI site and the XhoI site in pAO801 were eliminated.

pBSAGI5I was then digested with ClaI and the approximately 2.0 kbp fragment was isolated. The 2.0 kbp fragment has an approximately 1.0-kbp segment which comprises the P. pastoris AOX1 promoter and transcription initiation site, an approximately 700 bp segment encoding the hepatitis B virus surface antigen ("HBsAg") and an approximately 300 bp segment which comprises the P. pastoris AOX1 gene polyadenylation signal and site-encoding segments and transcription terminator. The HBsAg coding segment of the 2.0 kbp fragment is terminated, at the end adjacent the 1.0 kbp segment with the AOX1 promoter, with an EcoRI site and, at the end adjacent the 300 bp segment with the AOX1 transcription terminator, with a StuI site, and has its subsegment which codes for HBsAg oriented and positioned, with respect to the 1.0 kbp promoter-containing and 300 bp transcription terminator-containing segments, operatively for expression of the HBsAg upon transcription from the AOX1 promoter. The EcoRI site joining the promoter segment to the HBsAg coding segment occurs just upstream (with respect to the direction of transcription from the AOX1 promoter) from the translation initiation signal-encoding triplet of the AOX1 promoter.

For more details on the promoter and terminator segments of the 2.0 kbp, ClaI-site-terminated fragment of pBSAGI5I, see European Patent Application Publication No. 226,846 and Ellis et al., Mol. Cell Biol. 5, 1111 (1985).

Plasmid pAO801 was cut with ClaI and combined for ligation using T4 ligase with the approximately 2.0 kbp ClaI-site-terminated fragment from pBSAGI5I. The ligation mixture was used to transform E. coli MC1061 to ampicillin resistance, and transformants were screened for a plasmid of the expected size (approximately 5.8 kbp) which, on digestion with ClaI and BglII, yielded fragments of about 2.32 kbp (with the origin of replication and ampicillin-resistance gene from pBR322) and about 1.9 kbp, 1.48 kbp, and 100 bp. On digestion with BglII and EcoRI, the plasmid yielded an approximately 2.48 kbp fragment with the 300 bp terminator segment from the AOX1 gene and the HBsAg coding segment, a fragment of about 900 bp containing the segment from upstream of the AOX1 protein encoding segment of the AOX1 gene in the AOX1 locus, and a fragment of about 2.42 kbp containing the origin of replication and ampicillin resistance gene from pBR322 and an approximately 100 bp ClaI-BglII segment of the AOX1 locus (further upstream from the AOX1-encoding segment than the first mentioned 900 bp EcoRI-BglII segment). Such a plasmid had the ClaI fragment from pBSAGI5I in the desired orientation, in the opposite undesired orientation, there would be EcoRI-BglII fragments of about 3.3 kbp, 2.38 kbp and 900 bp.

One of the transformants harboring the desired plasmid, designated pAO802, was selected for further work and was cultured to yield that plasmid. The desired orientation of the ClaI fragment from pBSAGI5I in pAO802 had the AOX1 gene in the AOX1 locus oriented correctly to lead to the correct integration into the P. pastoris genome at the AOX1 locus of linearized plasmid made by cutting at the BglII site at the terminus of the 800 bp fragment from downstream of the AOX1 gene in the AOX1 locus.

pAO802 was then treated to remove the HBsAg coding segment terminated with an EcoRI site and a StuI site. The plasmid was digested with StuI and a linker of sequence:

5'-GGAATTCC-3'

3'-CCTTAAGG-5' was ligated to the blunt ends using T4 ligase. The mixture was then treated with EcoRI and again subjected to ligating using T4 ligase. The ligation mixture was then used to transform E. coli MC1061 to ampicillin resistance and transformants were screened for a plasmid of the expected size (5.1 kbp) with EcoRI-BglII fragments of about 1.78 kbp, 900 bp, and 2.42 kbp and BglII-ClaI fragment of about 100 bp, 2.32 kbp, 1.48 kbp, and 1.2 kbp. This plasmid was designated pAO803. A transformant with the desired plasmid was selected for further work and was cultured to yield pAO803.

Plasmid pAO804 was then made from pAO803 by inserting, into the BamHI site from pBR322 in pAO803, an approximately 2.75 kbp BglII fragment from the P. pastoris HIS4 gene. See, e.g., Cregg et al., Mol. Cell. Biol. 5, 3376 (1985) and European Patent Application Publication Nos 180,899 and 188,677. pAO803 was digested with BamHI and combined with the HIS4 gene-containing BglII site-terminated fragment and the mixture subjected to ligation using T4 ligase. The ligation mixture was used to transform E. coli MC1061 to ampicillin-resistance and transformants were screened for a plasmid of the expected size (7.85 kbp), which is cut by SalI. One such transformant was selected for further work, and the plasmid it harbors was designated pAO804.

pAO804 has one SalI-ClaI fragment of about 1.5 kbp and another of about 5.0 kbp and a ClaI-ClaI fragment of 1.3 kbp; this indicates that the direction of transcription of the HIS4 gene in the plasmid is the same as the direction of transcription of the ampicillin resistance gene and opposite the direction of transcription from the AOX1 promoter.

The orientation of the HIS4 gene in pAO804 is not critical to the function of the plasmid or of its derivatives with cDNA coding segments inserted at the EcoRI site between the AOX1 promoter and terminator segments. Thus, a plasmid with the HIS4 gene in the orientation opposite that of the HIS4 gene in pAO804 would also be effective for use in accordance with the present invention.

The invention has been described in detail with reference to particular embodiments thereof. It will be understood, however, that variations and modifications can be effected within the spirit and scope of the invention.

That which is claimed is:

1. A DNA fragment comprising one or more copies of an expression cassette that includes, in the direction of transcription, the following sequences of nucleotides:
   (i) a promoter region of a methanol responsive gene of a methylotrophic yeast;
   (ii) a sequence of nucleotides encoding a polypeptide consisting essentially of:
   (a) the *S. cerevisiae* alpha mating factor (AMF) pre-pro sequence, including the processing site: lys-arg, and
   (b) an insulin-like growth factor-1 (IGF-1) peptide; and
   (iii) a transcription terminator functional in *Pichia pastoris*,
   wherein:
   the sequences of nucleotides encoding the AMF sequence and the IGF-1 peptide are operationally associated, such that upon transcription and translation of the transcript, biologically active IGF-1 peptide is secreted;
   the promoter and terminator are operationally associated with the sequence of nucleotides encoding the polypeptide for transcription of the sequence of nucleotides;
   the promoter region directs methanol-induced transcription in *Pichia pastoris* of the sequence of nucleotides encoding the polypeptide; and
   the methylotrophic yeast is a species that is a member of a genus selected from the group consisting of Candida, Hansenula, Pichia, and Torulopsis that uses methanol as a sole carbon source.

2. The DNA fragment of claim 1, further comprising at least one selectable marker gene and a bacterial origin of replication.

3. A plasmid, comprising the DNA fragment of claim 2.

4. The DNA fragment of claim 1, wherein the sequence of nucleotides that encodes the IGF-1 peptide encodes a mature IGF-1 peptide that has the amino acid sequence set forth in FIG. 1.

5. A *Pichia pastoris* yeast cell transformed with the DNA fragment of claim 4.

6. The DNA fragment of claim 1, wherein said methylotrophic yeast is a strain of *Pichia pastoris*.

7. The DNA fragment of claim 6, wherein said methanol responsive gene of a methylotrophic yeast and the transcription terminator are derived from the *P. pastoris* AOX1 gene.

8. The DNA fragment of claim 7, further comprising 3'- and 5'-ends having sufficient homology with a target gene of a yeast host for said DNA fragment to effect site directed integration of said fragment into said target gene, wherein the yeast host is a species of Pichia that uses methanol as a sole carbon source.

9. The DNA fragment of claim 8, containing multiple copies of said expression cassette.

10. A *Pichia pastoris* cell transformed with the DNA fragment of claim 9.

11. A culture of viable *P. pastoris* cells, comprising cells of claim 10.

12. A *Pichia pastoris* cell transformed with the DNA fragment of claim 8.

13. A culture of viable *P. pastoris* cells comprising cells of claim 12.

14. The DNA fragment of claim 1, containing multiple copies of said expression cassette.

15. The DNA fragment of claim 14, wherein said multiple copies of said expression cassette are oriented in head-to-tail orientation.

16. A *Pichia pastoris* yeast cell transformed with the DNA fragment of claim 14.

17. A process for producing insulin-like growth factor-1 (IGF-1) peptides, comprising growing *Pichia pastoris* cells of claim 16 under conditions whereby IGF-1 peptide is expressed and secreted into the culture medium.

18. The process of claim 17, wherein said cells are grown in a medium containing methanol as a carbon source.

19. The process of claim 17, wherein said cells have the Mut+ phenotype.

20. The process of claim 17, wherein said cells have the Mut− phenotype.

21. The process of claim 17, wherein the initial pH of the culture medium is about 5 and decreases and is maintained at a pH of between about 2 and about 4 prior to, during and following induction of the methanol responsive promoter.

22. The process of claim 21, wherein the initial pH of the culture medium is about 5 and decreases and is maintained at a pH in the range of about 2–3.5 prior to, during and following induction of the methanol responsive promoter.

23. A *Pichia pastoris* yeast cell transformed with the DNA fragment of claim 1.

24. A culture of viable *Pichia pastoris* cells, comprising cells of claim 23.

25. A process for producing insulin-like growth factor-1 (IGF-1) peptides, comprising growing *Pichia pastoris* cells of claim 23 under conditions whereby IGF-1 peptide is expressed and secreted into the culture medium.

26. The process of claim 25, wherein said cells are grown in a medium containing methanol as a carbon source.

27. The process of claim 25, wherein said cells have the Mut+ phenotype.

28. The process of claim 25, wherein said cells have the Mut− phenotype.

29. The process of claim 25, wherein the initial pH of the culture medium is about 5 and decreases and is maintained at a pH of between about 2 and about 4 prior to, during and following induction of the methanol responsive promoter.

30. The process of claim 25, wherein the initial pH of the culture medium is about 5 and decreases and is maintained at a pH in the range of about 2–3.5 prior to, during and following induction of the methanol responsive promoter.

31. The DNA fragment of claim 1, wherein the promoter region is selected from the group of *Pichia pastoris* promoter regions of methanol responsive genes consisting of the promoter for the primary alcohol oxidase gene AOX1, the promoter region of the secondary alcohol oxidase gene AOX2, the promoter region for the dihydroxyacetone synthase gene DAS, the promoter for the P40 gene and the promoter for the catalase gene promoters that direct methanol-induced transcription in *Pichia pastoris* of the sequence of nucleotides encoding the polypeptide.

* * * * *